(12) United States Patent
Teruuchi et al.

(10) Patent No.: US 11,372,001 B2
(45) Date of Patent: Jun. 28, 2022

(54) ANTI-HUMAN IGG4 MONOCLONAL ANTIBODY AND METHODS OF MAKING AND USING SAME

(71) Applicant: NITTO BOSEKI CO., LTD., Fukushima (JP)

(72) Inventors: Yuya Teruuchi, Koriyama (JP); Yuri Matsuki, Tokyo (JP); Kazumitsu Inagaki, Koriyama (JP); Daisuke Sasaki, Koriyama (JP); Haruka Kashiwagura, Koriyama (JP)

(73) Assignee: NITTO BOSEKI CO., LTD., Fukushima (JP)

( * ) Notice: Subject to any disclaimer, the term of this patent is extended or adjusted under 35 U.S.C. 154(b) by 292 days.

(21) Appl. No.: 16/628,217

(22) PCT Filed: Jul. 5, 2018

(86) PCT No.: PCT/JP2018/025441
§ 371 (c)(1),
(2) Date: Jan. 2, 2020

(87) PCT Pub. No.: WO2019/009346
PCT Pub. Date: Jan. 10, 2019

(65) Prior Publication Data
US 2021/0140973 A1    May 13, 2021

(30) Foreign Application Priority Data

Jul. 6, 2017  (JP) .............................. JP2017-132841

(51) Int. Cl.
G01N 33/68    (2006.01)
C07K 16/42    (2006.01)
G01N 33/543   (2006.01)
G01N 33/545   (2006.01)

(52) U.S. Cl.
CPC ......... *G01N 33/6854* (2013.01); *C07K 16/42* (2013.01); *G01N 33/545* (2013.01); *G01N 33/54306* (2013.01); *C07K 2317/35* (2013.01); *C07K 2317/54* (2013.01); *C07K 2317/56* (2013.01); *C07K 2317/565* (2013.01); *C07K 2317/92* (2013.01)

(58) Field of Classification Search
CPC .............. G01N 33/6854; C07K 16/42; C07K 2317/54; C07K 2317/56; C07K 2317/565
See application file for complete search history.

(56) References Cited

U.S. PATENT DOCUMENTS

2009/0263915 A1  10/2009  Yoshida et al.
2015/0018529 A1  1/2015   Humphreys et al.

FOREIGN PATENT DOCUMENTS

| EP | 0 205 352 A2 | 12/1986 |
| EP | 0 516 529 A2 | 12/1992 |
| JP | 61-286754 A | 12/1986 |
| JP | 4-350559 A | 12/1992 |
| JP | 2001-501579 A | 2/2001 |
| JP | 2001-337092 A | 12/2001 |
| JP | 2017-132841 | 7/2017 |
| WO | WO 2008/012944 A1 | 1/2008 |
| WO | WO 2017/120222 A1 | 7/2017 |
| WO | WO 2010/151792 A1 | 12/2018 |
| WO | WO 2019/09346 | 1/2019 |

OTHER PUBLICATIONS https://www.ebi.ac.uk/chebi/searchId.do?chebiId=CHEBI:73505 (May 30, 2013). Accessed on the internet Dec. 23, 2021.*
https://www.mabtech.com/products/anti-human-igg4-antibody-mtg42-purified-3854-3. Accessed on the internet Dec. 30, 2021.*
https://www.biolegend.com/en-us/products/purified-anti-human-igg4-antibody-14561?GroupID= BLG13506. Accessed on the internet Dec. 30, 2021.*
https://www.sigmaaldrich.com/us/en/product/sigma/b3648, Accessed on the internet Dec. 30, 2021.*
https://www.genetex.com/Product/Detail/Mouse-Anti-Human-IgG4-Fc-antibody-HP6025-HRP/ GTX75819. Accessed on the internet Dec. 30, 2021.*
Deshpande V, et al. (2012) Modern Pathology. 25:1181-1192.*
Matsuki.Y., et al., "Performance evaluation of IgG4 measurement reagent 'N assay LA IgG4 Nittobo' in General-Purpose Automatic Analyzer," *Japanese Journal of Medicine and Pharmaceutical Science*, 75(7):849-858 (2018).
Vidarsson, G., et al., "IgG subclasses and allotypes: from structure to effector functions," *Frontiers in Immunology*, 5(520):1-17 (2014).
Jefferis, R., et al., "Evaluation of Monoclonal Antibodies Having Specificity For Human IgG Sub-Classes: Results Of An IUIS/WHO Collaborative Study," *Immunology Letters*, 10:223-252 (1985).
Harada, S., et al., "Evaluation of Production of Characterization of Monoclonal Antibodies to Human IgG of Four Subclasses," *Microbiol. Immunol.*, 33(7):579-592 (1989).
Usami, Y., et al., "Evaluation of basic performance of IgG4 quantitative reagent that can be used for measurement with general-purpose biochemical autmatic analyzer," *Japanese Journal of Clinical Laboratory Automation*, 39(4):629 (2014).

(Continued)

*Primary Examiner* — Robert S Landsman

(74) *Attorney, Agent, or Firm* — Crowell & Moring LLP

(57) ABSTRACT

Provided are: a monoclonal antibody against human IgG4, for which the epitope is present in the CH3 of human IgG4 given by SEQ ID NO: 4; a hybridoma that produces the monoclonal antibody; a method for detecting IgG4 using the monoclonal antibody; and a kit used in this method.

21 Claims, 8 Drawing Sheets
Specification includes a Sequence Listing.

(56) References Cited

OTHER PUBLICATIONS

Stone, J.H., et al., "IgG4-Related Disease," *N. Engl. J. Med.*, 366(6):539-551 (2012).

Khosroshahi, A., et al., "Spuriously Low Serum IgG4 Concentrations Caused by the Prozone Phenomenon in Patients With IgG4-Rleated Disease," *Arthritis & Rheumatology*, 66(1):213-217 (2014).

Davies, A., et al., "Structural Determinants of Unique Properties of Human IgG4-Fc," *J. Mol. Biol.*, 426:630-644 (2014).

Deshpande, V., et al., "Consensus statement on the pathology of IgG4-related disease," *Modern Pathology*, 25:1181-1192 (2012).

Hamilton, R., et al., "Epitope mapping of human immunoglobulin-specific murine monoclonal antibodies with domain-switched, deleted and point-mutated chimeric antibodies," *J. of Immun. Methods*, 158:107-122 (1993).

Kawa, S., "IgG4-Related Disease," *Center for Health, Safety and Environmental Management, Shinshu University*, 60(4):193-200 (2012).

International Search Report issued for PCT/JP2018/025441 dated Oct. 2, 2018 (in Japanese and English translation thereof).

Written Opinion issued for PCT/JP2018/025441 dated Sep. 9, 2018 (in Japanese and English translation thereof).

Extended European Search Report including supplementary European search Yeport and the European search opinion, received in European Patent Application No. 18828757.7 dated Feb. 10, 2021.

Koneczny, I., "A New Classification System for IgG4 Autoantibodies," *Frontiers in Immunology*, 9 (97):1-22 (2018).

Clark, M., "IgG Effector Mechanisms," *Chemical Immunology Antibody Engineering*, 65, 31 pages (1997).

Iwata, N., et al. "Anti-pituitary antibodies against corticotrophs in IgG4-related hypophysitis," *Pituitary*, 20(3):301-310 (2017; published online: Nov. 28, 2016).

Office Action and Search Report dated Apr. 26, 2022 received in the corresponding Taiwanese Patent Application No. 107123449 (in Taiwanese and including partial translation of the Office Action).

Kiyama, K., et al., "Screening for IgG4-type anti-nuclear antibodies in IgG4-related disease," BMC Muscoloskeletal Disorders, 16:129, 8 pages (2015).

\* cited by examiner

FIG.1
WITH ADAPTABILITY (5 CLONES)
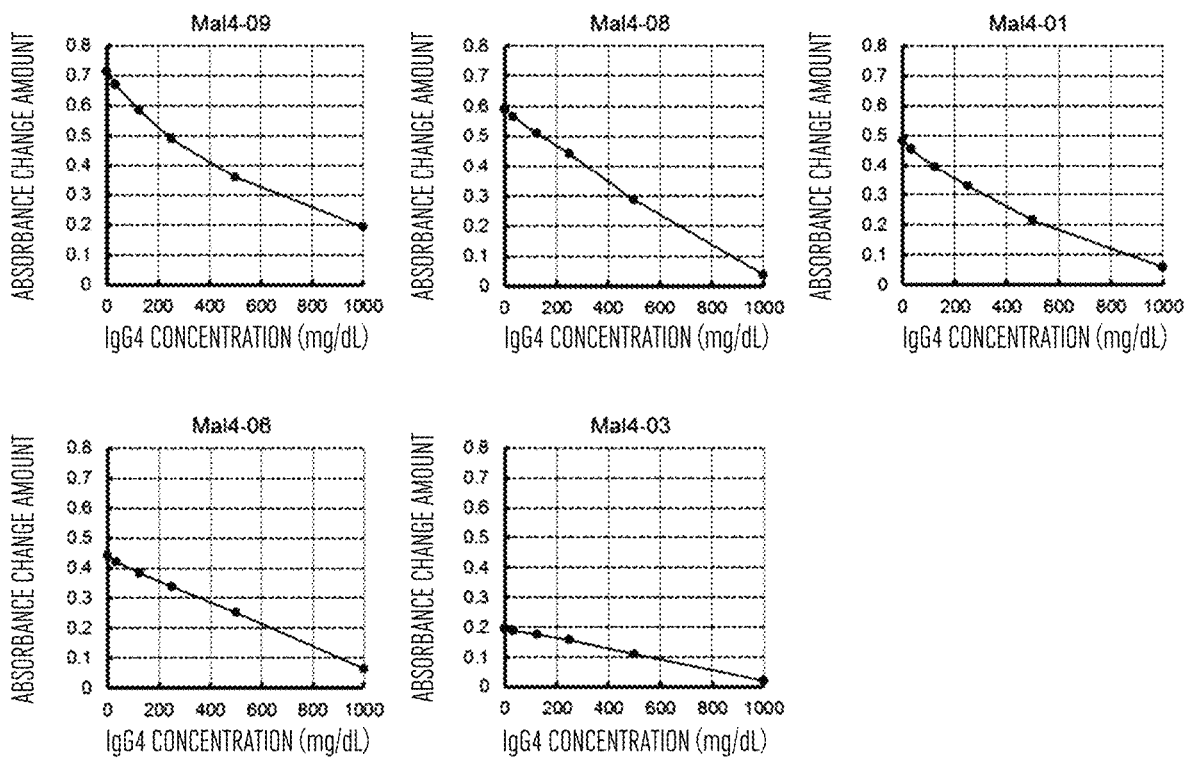
NO ADAPTABILITY (3 CLONES)
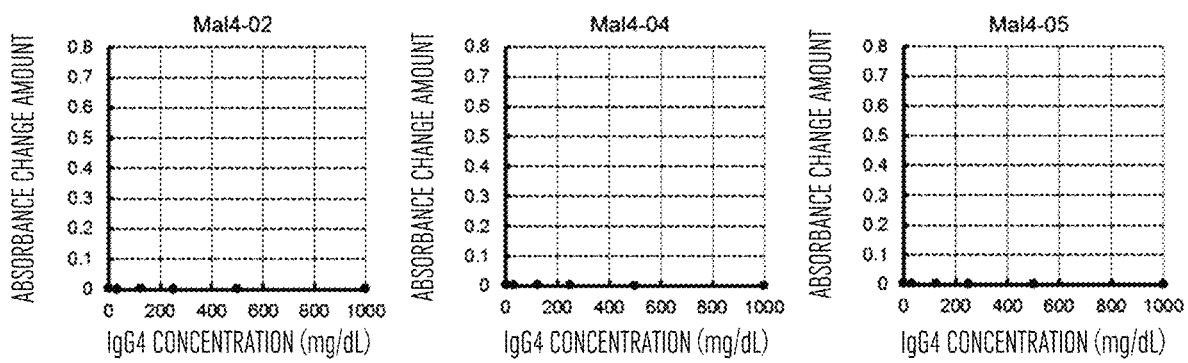

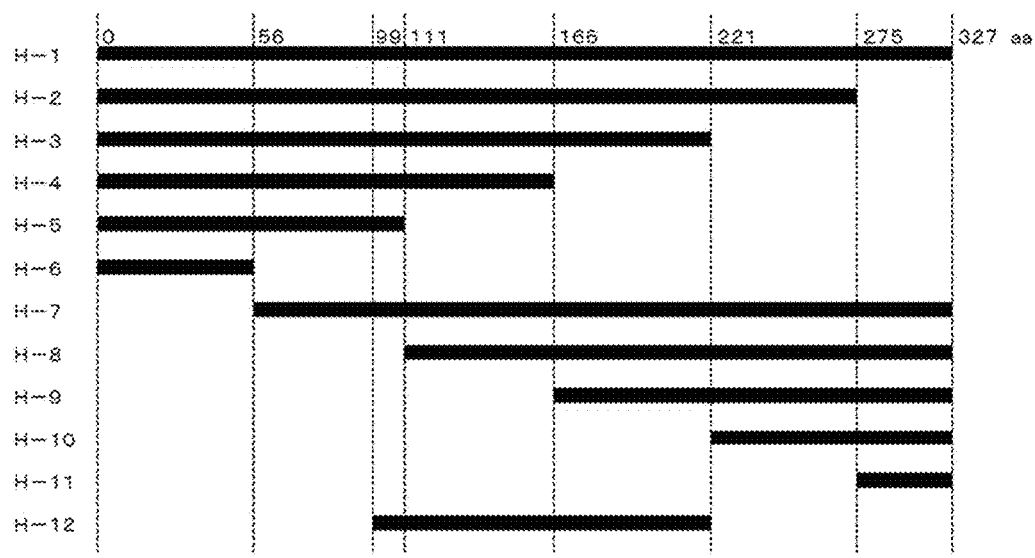

ANTI-HUMAN IGG4 MONOCLONAL ANTIBODY AND METHODS OF MAKING AND USING SAME

CROSS-REFERENCE TO RELATED APPLICATIONS

The present patent document is a National Stage application of International Patent Application Serial No. PCT/JP2018/025441, filed Jul. 5, 2018, which claims priority to Japanese Application No. 2017-132841, filed July 6, 2017, which are hereby incorporated by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "16325_4_SEQUENCE_LISTING_ST25" created on Dec. 31, 2019, and is 45.4 KB (46,521 bytes) in size. The sequence listing contained in this .txt file is part of the specification and is hereby incorporated by reference in its entirety.

TECHNICAL FIELD

The present invention relates to an anti-human IgG4 monoclonal antibody and a human IgG4 assay reagent comprising the antibody. With the anti-human IgG4 antibody of the present invention, human IgG4 in a sample can be specifically detected and assayed, which is extremely effective in the field of a diagnosis or a clinical examination for an IgG4-related disease.

BACKGROUND ART

In recent years, an IgG4-related disease has been proposed as a new disease concept. The IgG4-related disease may occur in various organs throughout the whole body, and is therefore required to discriminate from known various organ diseases. (Non-Patent Literature 1) The comprehensive criteria for diagnosing IgG4-related diseases were proposed in 2011 and set criteria according to which a hyper IgG4 syndrome is diagnosed when a value of IgG4 in blood is 135 mg/dL or more. A case of a subject with more than 5000 mg/dL of IgG4 in blood has reported, and inspection results of false low values have been considered problematic at the site of clinical examinations (Non-Patent Literature 2). In addition, a reagent for assaying IgG4 in blood is required to be applied to a versatile general automatic biochemical analyzer, which has been widely introduced in a hospital, a clinical examination center, and the like.

Regarding application of a reagent for assaying IgG4 in blood to a versatile automatic analyzer, the following two issues can be mentioned.

IgG4 is a heterotetramer molecule with a molecular weight of about 146000, and an antibody may be preferably used for detecting such a molecule.

Accordingly, the first issue can be specificity of an antibody which is an important constituent element of a reagent for the assay. IgG4 is one of IgG subclasses and has been known to have high homologies with IgG1, IgG2, and IgG3, i.e. the other subclasses (Non-Patent Literatures 3 and 4). In general, IgG1, IgG2, IgG3, and IgG4 is present in a ratio of 65%, 23%, 8%, and 4% in serum of a healthy person, respectively, and reference ranges of IgG1, IgG2, IgG3, and IgG4 in the healthy person is 351 to 962, 239 to 838, 8.5 to 140, and 4.5 to 117 (mg/dL), respectively. An amount ratio of IgG4 is small, and it is therefore necessary to produce an antibody having so excellent specificity as to be capable of reacting with only IgG4.

As an assay method with an antibody, used are an indirect antibody method such as an indirect enzyme-antibody method (enzyme-linked immunosorbent assay (ELISA) method), an indirect fluorescent antibody method and a chemiluminescent enzyme immunoassay method (CLEIA method); an immunodiffusion method such as a single radial immunodiffusion (SRID) method and a double immunodiffusion (DID) method; and a latex (particle) agglutination method classified into immunoturbidimetry (TIA) or immunonephelometry (NIA). However, methods currently widely utilized at the site of the clinical examinations are immunoturbidimetry (TIA) and immunonephelometry (NIA) such as a latex (particle) agglutination method, which reply on detecting agglutination based on an antigen-antibody binding, and which is capable of detecting a molecule of interest at a low concentration.

However, in a case where an antigen concentration in a sample such as blood or urine significantly exceeds an assay range, agglutination suppression may be induced by an excessive antigen (referred to as zone phenomenon or prozone phenomenon). As a result, an measured value may be a false low value, which may cause an incorrect diagnosis. Regarding IgG4, as described above, a case has been reported in which a concentration difference between a healthy person and a patient with a hyper IgG4 syndrome was almost 1000 times, and a prozone phenomenon actually occurred in the case of using a reagent for assaying IgG4. (Non-Patent Literature 2)

Accordingly, as the second issue, a reagent for assaying IgG4 in blood is also required to assay IgG4 at a high concentration.

Regarding the first issue, a monoclonal antibody against a human IgG4 has been known (Patent Literature 1). The monoclonal antibody has high specificity to IgG4 among the IgG subclasses. However, a recognition site (epitope) of the monoclonal antibody is generally one, and it may not be suitable to form antibody-antigen agglutination. An IgG4-specific monoclonal antibody applicable to an assay for IgG4 by immunoturbidimetry has not been known. A reagent for assaying IgG4 comprising a monoclonal antibody and applicable to a versatile automatic analyzer has not been known, either.

A solution to the issue is to render a monoclonal antibody artificially multivalent, which also solves the second issue. For example, Patent Literature 2 describes a method of biotinylating a monoclonal antibody and forming a multimer with streptavidin, Patent Literature 3 describes a method of forming a multimer with protein A or an anti-immunoglobulin antibody, and Patent Literature 4 describes a method of immobilizing a monoclonal antibody onto an insoluble carrier. However, all the methods comprise complicated steps for forming a multivalent monoclonal antibody, and, in particular, it is difficult to constantly control a valency of an antibody. Cost and time are therefore required to maintain quality and function of a reagent based on immunoturbidimetry as an assay principle and applicable to a versatile automatic analyzer.

In antiserum obtained by immunizing a goat, a sheep, or a rabbit against a human IgG4 based on a general animal experimental technique for obtaining a polyclonal antibody, most of produced antibodies are directed to a portion common to the IgG subclasses, and a step of adsorbing an antibody capable of reacting with the other subclasses other than IgG4 is required. Very complicated steps for purification are therefore required to obtain a specific antibody against IgG4. There is a concern that the relative or absolute abundance of a specific antibody against IgG4 contained in the antiserum and the above-mentioned steps for purification would make a yield of a specific antibody against IgG4 of interest very low.

A method for obtaining a polyclonal antibody with high specificity to any one of IgG subclasses has been known (Patent Literature 5). According to this method, it is possible to obtain an antigen-specific polyclonal antibody by immune tolerance without the above-mentioned steps for purification. There are, however, individual differences in degree of induction of the immune tolerance among immunized animals, and it takes time to induce immune tolerance. A large amount of animals therefore need to be immunized to constantly obtain a specific antibody against IgG4 of interest, and it is hard to say that it is an appropriate method in the viewpoint of costs and animal welfare.

CITATION LIST

Patent Literature

PATENT LITERATURE 1: JP61-286754A
PATENT LITERATURE 2: JP04-350559A
PATENT LITERATURE 3: JP2001-337092A
PATENT LITERATURE 4: WO 2008/012944
PATENT LITERATURE 5: JP2001-501579A

Non-Patent Literature

NON-PATENT LITERATURE 1: N Engl J Med 2012; 366: 539-551
NON-PATENT LITERATURE 2: Arthritis Rheumatol. 2014 January; 66 (1): 213-7
NON-PATENT LITERATURE 3: J Mol Biol. 2014 Feb. 6; 426 (3): 630-44
NON-PATENT LITERATURE 4: Front Immunol. 2014; 5: 520
NON-PATENT LITERATURE 5: Consensus statement on the pathology of IgG4-related disease (Modern Pathology 2012 25, 1181-1192)
NON-PATENT LITERATURE 6: Epitope mapping of human immunoglobulin specific murine monoclonal antibodies with domain switched deleted and point mutated chimeric antibodies (Journal of Immunological Methods 158 1993 107-122)

SUMMARY OF INVENTION

Technical Problem

In view of these issues, an object of the present invention is to provide a monoclonal antibody with higher specificity to and affinity with IgG4, a hybridoma producing the monoclonal antibody, a method for detecting IgG4 with the monoclonal antibody, and a kit used for the method.

Solution to Problem

An immunological particle agglutination method (latex (particle) agglutination method) is a method for assaying an antigen of interest by immobilizing an antibody onto an insoluble carrier, mixing a sample comprising the antigen of interest with the insoluble carrier to cause an immunological agglutination reaction based on an antigen-antibody reaction. In the method, in order to increase detection sensitivity, plural types of antibodies that recognize various epitopes, such as polyclonal antibodies, are preferably used. This is because that agglutination occurs when a plurality of antibodies (or insoluble carriers) bind to one antigen molecule. Instead, each antibody molecule may include ones with low affinity.

Meanwhile, an immunological particle agglutination inhibition method (latex (particle) agglutination inhibition method) is a method of assaying an amount of antigen of interest, the method being performed by mixing an insoluble carrier on which an antigen is immobilized, a free antibody against the antigen, and a sample containing the antigen to cause competition between the antigen immobilized onto the insoluble carrier and the antigen contained in the sample, thereby inhibiting agglutination formation. In the immunological particle agglutination inhibition method, a prozone phenomenon does not occur even in a case where an antigen concentration greatly exceeds an assay range, and the method is thus an ideal method to avoid a risk of a prozone phenomenon as an assay principle when the method is applied to a versatile automatic analyzer. Polyclonal antibodies are however not suitable for such a method. This is because there are a plurality of epitopes for the antibodies, and agglutination through an antigen in a sample and an antigen carried onto a carrier easily occurs. Sensitivity of an assay system decreases as compared to a monoclonal antibody, which recognizes a single epitope, and it may be difficult to draw a decay curve.

In view of the foregoing, the inventors of the present invention, as a result of intensive studies, have succeeded in producing a monoclonal antibody suitable for an immunological particle agglutination inhibition method (latex (particle) agglutination inhibition method) for detecting human IgG4, thereby completing the present invention.

That is, the present invention provides the following [1] to [21].

[1] A monoclonal antibody specifically binding to human IgG4, wherein an epitope to which the monoclonal antibody binds is present in an amino acid sequence at positions 221 to 327 of a human IgG4 heavy chain constant region represented by SEQ ID NO: 4, and has glutamic acid at position 299;

[2] The monoclonal antibody according to [1], wherein the monoclonal antibody binds to the human IgG4 with a dissociation constant of $5.0 \times 10^{-10}$ or less;

[3] A monoclonal antibody against human IgG4, or preferably the monoclonal antibody according to [1] or [2], comprising a heavy chain variable region and a light chain variable region, wherein complementarity determining regions (CDR) 1, 2, and 3 of the heavy chain variable region consists of amino acid sequences represented by SEQ ID NOS: 9, 10, and 11, respectively, and CDRs 1, 2, and 3 of the light chain variable region consists of amino acid sequences represented by SEQ ID NOS: 12, 13, and 14, respectively;

[4] The monoclonal antibody according to [3], wherein the heavy chain variable region comprises an amino acid sequence of SEQ ID NO: 5, and the light chain variable region comprises an amino acid sequence of SEQ ID NO: 6;

[5] The monoclonal antibody according to [4], wherein the monoclonal antibody is produced by a hybridoma MaI4-08.

[6] A monoclonal antibody against human IgG4, or preferably the monoclonal antibody according to [1] or [2], comprising a heavy chain variable region and a light chain variable region, wherein complementarity determining regions (CDRs) 1, 2, and 3 of the heavy chain variable region consists of amino acid sequences represented by SEQ ID NOS: 15, 16, and 17, respectively, and CDRs 1, 2, and 3 of the light chain variable region of the antibody consists of amino acid sequences represented by SEQ ID NOS: 18, 19, and 20, respectively;

[7] The monoclonal antibody according to [6], wherein the heavy chain variable region comprises an amino acid sequence of SEQ ID NO: 7, and the light chain variable region comprises an amino acid sequence of SEQ ID NO: 8;

[8] The monoclonal antibody according to [7], wherein the monoclonal antibody is produced by a hybridoma MaI4-09.

[9] A multivalent antibody or a multivalent antibody fragment comprises two or more antigen (recognition) binding sites of the monoclonal antibody according to any one of [1] to [8] per molecule, and more preferably a bivalent antibody or a bivalent antibody fragment comprises two antigen (recognition) binding sites of the monoclonal antibody according to any one of [1] to [8] per molecule;

[10] The antibody fragment according to [9], wherein the antibody fragment is F(ab')2.

[11] A method for detecting human IgG4 in a sample with the monoclonal antibody according to any one of [1] to [8] or the antibody fragment according to [9] or [10];

[12] The method according to [11], wherein the method is immunoturbidimetry or immunonephelometry;

[13] The method according to [12], wherein the method is an immunological particle agglutination method;

[14] The method according to [12], wherein the method is an immunological particle agglutination inhibition method;

[15] The method according to [11], wherein the method is immunohistochemistry (IHC) staining;

[16] The method according to [11], wherein the method is performed with flow cytometry.

[17] The method according to [14];

[18] A kit for detecting human IgG4, comprising the monoclonal antibody according to any one of [1] to [8] or the antibody fragment according to [9] or [10].

[19] A kit for the method according to [14] or [17], the kit comprising:
  (1) the monoclonal antibody according to any one of [1] to [8] or the antibody fragment according to [9] or [10];
  (2) an isolated human IgG4 or a peptide fragment thereof; and
  (3) an insoluble carrier.

[20] The kit according to [19], wherein (2) the isolated human IgG4 or the peptide fragment thereof is adsorbed onto (3) the insoluble carrier.

[21] The kit according to [19] or [20], wherein (3) the insoluble carrier is a latex particle.

[22] The method according to any one of [11] to [17], wherein the method is performed to assist a diagnosis of an IgG4-related disease.

[23] The kit according to any one of [18] to [21], wherein the kit is used for a diagnosis of an IgG4-related disease.

[24] An isolated peptide consisting of all or a part of an amino acid sequence at positions 221 to 327 of a human IgG4 heavy chain constant region represented by SEQ ID NO: 4, and comprising glutamic acid at position 299.

According to an embodiment of the present invention, IgG4 in a biological sample can be efficiently detected and quantified, which can assist in diagnosis of various diseases. According to an embodiment of the present invention, it is possible to assist a diagnosis of an IgG4-related disease, which is a systemic and chronic inflammatory disease characterized by a high serum IgG4 level and marked IgG4-positive plasma cell invasion of affected organs. Examples of these diseases, but not limited thereto, include Mikulicz disease, Kuttner tumor, dacryadenitis, IgG4-related eye disease, IgG4-related respiratory disease, inflammatory pseudotumor, mediastinal fibrosis, enteritis, sclerosing cholangitis, IgG4-related liver disease, autoimmune pancreatitis (AIP), IgG4-related kidney disease, retroperitoneal fibrosis, prostatitis, autoimmune hypophysitis, thyroiditis, hypertrophic pachymeningopathy, IgG4-related lymphadenopathy, arthritis, inflammatory abdominal aneurysm, and periarteritis.

BRIEF DESCRIPTION OF DRAWINGS

FIG. 1 shows the results of evaluating adaptability of selected clones to an immunological particle agglutination inhibition method.

FIG. 2 shows absorbance of the reaction of the MaI4-08-produced antibody with each human globulin by ELISA.

FIG. 3 shows absorbance of the reaction of the MaI4-09-produced antibody with each human globulin by ELISA.

FIG. 4 shows absorbance change in the cases of mixing and reacting a standard sample of human IgG4, a MaI4-08-produced antibody-containing buffer solution (first reagent), and a human IgG4-sensitized latex-containing buffer solution (second reagent). As standard samples, standard human serums with human IgG4 concentrations adjusted to 1.6, 6.3, 12.5, 25, and 50 mg/dL were used. In the assay, a specimen sample is diluted 20-fold and then assayed. The final standard sample concentration were therefore set to 20-fold higher, namely 31.3, 125, 250, 500, and 1000 mg/dL. The final concentrations of all samples described later are set to 20-fold ones.

FIG. 5 shows absorbance change in the cases mixing and reacting a standard sample of human IgG4, a MaI4-09-produced antibody-containing buffer solution (first reagent), and a human IgG4-sensitized latex-containing buffer solution (second reagent). Other conditions are the same as those in FIG. 4.

FIG. 6 shows absorbance change in the cases of mixing and reacting a standard sample of human IgG4, a MaI4-05-produced antibody-containing buffer solution (first reagent), and a human IgG4-sensitized latex-containing buffer solution (second reagent). Other conditions are the same as those in FIG. 4.

FIG. 7 shows absorbance change in the cases of mixing and reacting a standard sample of human IgG4, a HP6025-containing buffer solution (first reagent), and a human IgG4-sensitized latex-containing buffer solution (second reagent). Other conditions are the same as those in FIG. 4.

FIG. 8 shows measured values in the case of mixing and reacting a series of diluted human IgG4 samples in the range of 0 to 1000 mg/dL, a MaI4-08-produced antibody-containing buffer solution (first reagent), and a human IgG4-sensitized latex-containing buffer solution (second reagent).

FIG. 9 shows measured values in the case of mixing and reacting a series of diluted human IgG4 samples in the range of 0 to 1000 mg/dL, a MaI4-09-produced antibody-containing buffer solution (first reagent), and a human IgG4-sensitized latex-containing buffer solution (second reagent).

FIG. 10 shows measured values in the case of mixing and reacting a series of diluted human IgG4 samples in the range of 0 to 8000 mg/dL, a MaI4-08-produced antibody-containing buffer solution (first reagent), and a human IgG4-sensitized latex-containing buffer solution (second reagent).

FIG. 11 shows measured values in the case of mixing and reacting a series of diluted human IgG4 samples in the range of 0 to 8000 mg/dL, a MaI4-09-produced antibody-containing buffer solution (first reagent), and a human IgG4-sensitized latex-containing buffer solution (second reagent).

FIG. 12 shows measured values in the cases of mixing and reacting 3000 mg/dL of human IgG1, human IgG2, human IgG3 or human IgG4 sample, a MaI4-08-produced antibody-containing buffer solution (first reagent), and a human IgG4-sensitized latex-containing buffer solution (second reagent).

FIG. 13 shows measured values in the cases of mixing and reacting 3000 mg/dL of human IgG1, human IgG2, human IgG3 or human IgG4 sample, a MaI4-09-produced antibody-containing buffer solution (first reagent), and a human IgG4-sensitized latex-containing buffer solution (second reagent).

FIG. 14 illustrates an alignment between the amino acid sequence H1 (P01861, SEQ ID NO: 4) of a human IgG4 heavy chain constant region obtained from Uniprot and the amino acid sequences of peptides H2 to 12 each obtained by partially deleting the sequence H1. Positions 99 to 110 indicate a hinge region.

FIG. 15 illustrates an alignment between the amino acid sequence (H-10) of the CH3 region at positions 221 to 327 of the amino acid sequence (SEQ ID NO: 4) of a human IgG4 heavy chain constant region and the amino acid sequences (H-31 to H-39) obtained by substituting a part of H-10 with corresponding amino acids (shown in bold) of a human IgG1 heavy chain constant region.

DESCRIPTION OF EMBODIMENTS

Figure 2:
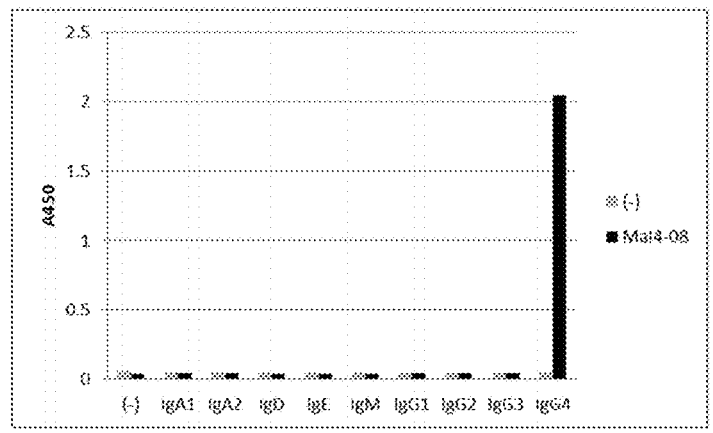
FIG. 2 shows the results of evaluating specificity of a MaI4-08 antibody by ELISA.

A monoclonal antibody according to an embodiment of the present invention is produced by, for example, a hybridoma obtained by immunizing an animal with a purified human IgG4 as an immunogen and fusing a cell producing an anti-human IgG4 antibody produced by the animal with a bone marrow tumor cell. The animal to be used is not limited, and examples of animals other than humans include a mouse, a rat, a guinea pig, a hamster, and a rabbit. In particular, a mouse, IgG subtypes of which are IgG1, IgG2a, IgG2b, and IgG3, is preferable.

The hybridoma can be obtained by the following method. That is, human IgG4 is mixed with a conventional adjuvant such as Freund's complete or incomplete adjuvant, aluminum hydroxide adjuvant, or pertussis adjuvant to prepare an adjuvant solution for sensitization, and this liquid is administered to an animal such as a mouse or a rat intraperitoneally, subcutaneously or via the tail vein, in several portions every 1-3 other weeks to immunize the animal. The amount of the antigen for sensitization is in the range of 1 µg to 100 mg, but is preferably about 50 µg in general. The number of immunizations is generally 2 to 7, but various methods are known. Subsequently, a cell producing antibody derived from the spleen or the like is fused with a cell having proliferative ability such as a bone marrow tumor cell (myeloma cell) or the like in a test tube. The antibody-producing cell can be obtained from the spleen or the like of a mouse, a nude mouse, a rat, or the like.

As the fusion method, the Kohler and Milstein method with polyethylene glycol (PEG) (Nature. 256, 495. 1975) is well known. The fusion can be also carried out by Sendai virus or an electrofusion method.

A method of selecting a hybridoma that produces an antibody that recognizes a human IgG4 from the fused cells can be carried out as follows. That is, the hybridoma is selected from colonies formed by cells surviving in a HAT medium and a HT medium by subjecting the fused cells to a limiting dilution method. In a case where an antibody against a human IgG4 is contained in a supernatant of a medium which cultured colonies of the fused cells seeded into a 96-well plate or the like, a clone capable of producing a monoclonal antibody against a human IgG4 can be selected by an ELISA method in which the supernatant is placed on an assay plate on which the human IgG4 is immobilized, and after the reaction, a labeled secondary antibody such as HRP labeled anti-mouse immunoglobulin antibody is reacted with the antibody. As a labeling substance of the labeled antibody, an enzyme other than HRP, such as alkaline phosphatase, a fluorescent substance, a radioactive substance, and the like, can be used. In addition, specific antibodies against human IgG4 can be screened by simultaneously carrying out, as a control, ELISA with an assay plate on which only BSA, which is a blocking agent, is bound. That is, a clone which is positive on a plate having a human IgG4 but negative in ELISA with BSA can be selected.

A hybridoma according to an embodiment of the present invention is in particular preferably a hybridoma that produces an antibody that binds to a human IgG4 but does not bind to other human immunoglobulins (other IgGs, e.g. IgG1, IgG2 and IgG3, IgA, e.g. IgA1 and IgA2, IgD, IgE, and IgM) among hybridomas that produce a monoclonal antibody recognizing human IgG4.

Here, "binds to human IgG4 but does not bind to other human immunoglobulins" in brief refers to the following: for example, in an ordinary ELISA under the same assay conditions except for the conditions mentioned below, a ratio of absorbance to a control (blank) which does not contain any human immunoglobulin is 40 or more, preferably 50 or more, and more preferably 100 or more in a case where a human IgG4 is contained as a solid phase antigen, whereas a ratio of absorbance to a control (blank) which does not contain any human immunoglobulin is 5 or less and preferably 2 or less in a case where IgG other than human IgG4 is contained as a solid phase antigen.

The term also means that the antibody exhibits higher binding affinity with human IgG4 than other human immunoglobulins, which can be evaluated with a binding rate constant and a dissociation constant. Specifically, an antibody according to a preferred embodiment of the present invention binds to a specific epitope in a human IgG4 heavy chain constant region at a binding rate constant of $4.0\times10^5$ or more and generally $4.0\times10^5$ to $6.0\times10^5$ and a dissociation constant of $5.0\times10^{-10}$ or less and generally $5.0\times10^{-10}$ to $3.0\times10^{-10}$.

The hybridoma may be cultured on a medium used for ordinary cell culture, such as α-MEM, RPMI1640, ASF, or S-clone, and a monoclonal antibody can be recovered from the supernatant of the culture medium. Alternatively, an animal from which the hybridoma cell has been derived, such as a nude mouse, is previously treated with pristine, the cell is intraperitoneally injected into the animal to cause accumulation of ascites, and the monoclonal antibody is recovered from the ascites.

A method for recovering the monoclonal antibody from the supernatant or the ascites may be a conventional method. An example of the above method includes a salting-out treatment with ammonium sulfate, sodium sulfate and the like, chromatography, ion exchange chromatography, or affinity chromatography with protein A, protein G and the like.

An immunoassay method with a monoclonal antibody according to an embodiment of the present invention allows a human IgG4 in a specimen to be detected with high sensitivity and specificity. Examples of a specimen include blood, serum, plasma, and the like taken or isolated from a subject. The specimen may be a biopsy sample from a lesion tissue of the body, such as pituitary gland, lacrimal gland, salivary gland, thyroid, prostate, bronchial epithelium, alveolar septum, pancreatic duct, retroperitoneum, bile duct wall, and rheumatoid arthritis synovium.

The "immunoassay method" refers to a biochemical assay for detecting a level of a substance contained in a biological sample through a reaction between an antibody and an antigen.

Examples of a detection system for the "immunoassay method" with a monoclonal antibody according to an embodiment of the present invention include a sandwich ELISA method, a chemiluminescent enzyme immunoassay method (CLEIA method), a fluorescent immunoassay method (FIA method), a latex (particle) agglutination method (turbidimetry method), and a latex (particle) agglutination inhibition method is more preferable.

The "ELISA method" means Enzyme-Linked ImmunoSorbent Assay (ELISA)/EnzymeImmuno Assay (EIA), and refers to a method for detecting or quantifying a concentration of a substance contained in a sample through an enzyme reaction. A substance of interest is detected and assayed by using color development or light emission based on the enzyme reaction as a signal.

A "competitive ELISA method" means an ELISA method for assaying at what ratio a "labeled antigen" and an "antigen present in the sample" bind to the antibody under a competitive condition.

The "immunoturbidimetry" is a method for assaying an amount of an antigen contained in a specimen, the method being performed by reacting the antigen with an antibody to form a precipitate of an immune complex, irradiating the agglutination with light, and measuring an attenuation (absorbance) of the irradiated light due to scattering with an automatic analyzer.

The "immunonephelometry" is a method of detecting an antigen contained in a specimen, the method being performed by reacting an antibody with an antigen to form a precipitate of an immune complex, irradiating the complex with light, and measuring scattered light.

The "latex (particle) agglutination method" is a method for detecting an antigen by immobilizing an antibody onto latex particles, agglutinating the latex particles in the presence of an antigen and observing the agglutination.

The "latex (particle) agglutination inhibition method" is a method on indirectly detecting "the antigen present in the sample" comprising immobilizing an antigen onto latex particles, and detecting at what ratio "the antigen bound to the latex particles" and "the antigen present in the sample" bind to the antibody under a competitive condition through the aggregate of the latex particle.

In the both methods, for the observation of the aggregate, an attenuation (absorbance) of irradiated light due to scattering may be measured (immunoturbidimetry), or scattered light may be measured (immunonephelometry).

In an embodiment of the present invention, "the antigen bound to the latex particles" may not be necessarily the same molecule as "the antigen present in the sample", and in terms of the binding with the antibody according to the present invention or an antigen-binding fragment thereof it may just be a molecule that competes with "the antigen present in the sample". In other words, in a case where the antibody according to the present invention is used for "the latex (particle) agglutination inhibition method", it is preferable that "the antigen bound to the latex particles" and "the antigen present in the sample" each comprise an epitope to which the antibody binds.

The epitope refers to a part of an antigen recognized by an antibody. A human IgG4 is a heterotetramer molecule having a molecular weight of about 146000, and composed of two molecules of light chains consisting of a variable region VL and a constant region CL, and two molecules of heavy chains consisting of a variable region VH, a constant region CH1, a hinge region, a constant region CH2, and a constant region CH3. The antibody does not recognize an entire antigen, but recognizes only a relatively small part of an antigen to bind thereto. In order to function as an epitope, at least 10 amino acid residues in length and more preferably 5 amino acid residues in length are required. The antibody binding site is called an "epitope" or an "antigenic determinant".

An antibody according to an embodiment of the present invention is required to recognize IgG4 but not IgG1, IgG2, or IgG3. Since light chains are common to IgG1 to IgG4, it is preferable that an epitope is in a heavy chain, in particular, a heavy chain constant region. Heavy chain constant regions of IgG1, IgG2, IgG3, and IgG4 are represented by SEQ ID NOS: 1, 2, 3, and 4, respectively, and a portion at which homology between SEQ ID NOS: 1 to 3 and SEQ ID NO: 4 is low is preferably selected as an epitope. As demonstrated in Examples later, in particular, it is preferably an epitope present in a human IgG4 CH3 region, more specifically an epitope present within an amino acid sequence at positions 221 to 327 of a human IgG4 heavy chain constant region represented by SEQ ID NO: 4, and comprising glutamic acid at position 299, in terms of achieving a specific binding to IgG4 without an interaction with other IgG subclasses. In other words, an epitope to which the antibody binds according to a preferred embodiment of the present invention consists of all or a part of an amino acid sequence at positions 221 to 327 of a human IgG4 heavy chain constant region represented by SEQ ID NO: 4, and comprises glutamic acid at position 299. Therefore, according to another preferred embodiment of the present invention, there is provided a peptide comprising an epitope, and more particularly, a peptide consisting of all or a part of an amino acid sequence at positions 221 to 327 of a human IgG4 heavy chain constant region represented by SEQ ID NO: 4, and comprising glutamic acid at position 299. The part of the amino acid sequence generally consist of 5 to 50 amino acids, and preferably 10 to 30 amino acids.

In the "latex (particle) agglutination method", agglutination usually does not occur without a plurality of monoclonal antibodies (i.e., polyclonal antibody) directed to different epitopes. However, since IgG4 itself is a dimer of a heterodimer consisting of a light chain and a heavy chain, there may be a monoclonal antibody used for agglutination reaction. In addition, if a plurality of antibody molecules are adsorbed onto latex particles, agglutination can occur even in a case where the antibody molecules are a monovalent antibody molecule (one antigen (recognition) binding site per molecule).

An example of the "monovalent antibody" includes a Fab fragment that can be obtained by treating a natural antibody with papain or a single-chain variable fragment (scFV) obtained by binding a light chain variable region and a heavy chain variable region in genetic engineering.

On the other hand, in the "latex (particle) agglutination inhibition method", a polyclonal antibody is not suitable, because reactions in an assay system may vary in a case of using a plurality of antibodies having different binding constants, epitopes, and specificities, such as a polyclonal antibody.

In addition, a monovalent antibody molecule is also not suitable, because where an antibody to be used is a monovalent antibody molecule, an agglutination reaction between latex particles through the antibody (adsorbed to antigen) does not occur. Two or more antigen (recognition) binding sites per molecule are required, and wild type immunoglobulins (IgG (divalent)), IgA (tetravalent), IgD (divalent), IgE (divalent), and IgM (decavalent)), F(ab')2 (divalent) that can be obtained by pepsin treatment, or a multimer of a "monovalent antibody" is required.

The "antigen (recognition) binding site" refers to a minimum site of an antibody that can bind to an antigen. It, but not limited to, refers to a site comprising complementarity determining regions (CDRs) of a heavy chain and a light chain. The antigen (recognition) binding site may have a $V_L$ region, a light chain variable region, and a $V_H$ region, a heavy chain variable region. These regions may be bound to each other genetically or through an SS bond.

Generally, latex refers to a colloidal aqueous dispersion of a polymer resin, but the "latex particle" as used herein refers to a polymer resin having a uniform particle size. Any latex particle used in a general immunoassay method may be used, but a latex particle made of polystyrene as a main material is preferable.

A particle size of the latex particle used in the present application is 50 nm to 500 nm, preferably 75 nm to 306 nm, and more preferably 100 nm to 111 nm.

When a method according to an embodiment of the present invention is implemented, the method is performed with a kit for immunoassay of a human IgG4, comprising (1) an antibody of the present invention, (2) an isolated human IgG4 or a peptide fragment thereof, and (3) a solid support.

In the kit, the solid support and the isolated human IgG4 or the peptide fragment solution thereof may be separately prepared, and when IgG4 is assayed, an antibody may be adsorbed on the solid support. Alternatively, an antibody adsorbed on the solid support in advance may be provided. The kit preferably comprises a washing solution to remove components un-adsorbed on the solid support after an isolated human IgG4 in a specimen or a peptide fragment thereof is bound to an antibody. An example of the washing solution can include a Tris buffer solution containing a surfactant.

In addition, the kit of the present invention can further comprise a specimen dilute solution, if appropriate. The specimen dilute solution, for example, includes a buffer solution such as Tris and the like. Such a buffer solution may contain a chelating agent such as EDTA.2Na and a mineral salt such as sodium chloride, if appropriate.

As mentioned above, "an isolated human IgG4 or a peptide fragment thereof" is used as the "antigen bound to the latex particle". The isolated human IgG4 or the peptide fragment thereof is therefore required to comprise an epitope to which the antibody of the present invention binds. An isolated and purified natural IgG4 molecule may be used, or a "peptide fragment" genetically engineered, for example, obtained by cloning a part or the whole of a human IgG4 light chain or heavy chain constant region, may be used. A part or the whole of the human IgG4 heavy chain constant region may include a part or the whole of the amino acid sequence of SEQ ID NO: 4.

In an embodiment of the present invention, IgG4 can be assayed by a sandwich ELISA method with a monoclonal antibody of the present invention. In this case, the assay can be implemented additionally using another monoclonal antibody against another IgG4, other than the antibody of the present invention. A specific example of the method for assaying IgG4 by sandwich assay is as follows. First, an antibody of the present invention as a primary antibody is adsorbed on a solid support such as a plate, the primary antibody is reacted with IgG4 in a specimen such as serum, and the solid support is cleaned. The adsorbed IgG4 and a biotinized secondary antibody such as a biotinized different monoclonal antibody or a polyclonal antibody against the IgG4 are reacted, the reactant is reacted with peroxidase-labeled streptavidin, and then a peroxidase enzyme reaction and a coloring reaction are carried out, thereby detecting IgG4. Alternatively, the same assay can be carried out using a secondary antibody directly labeled with an enzyme such as peroxidase and alkaline phosphatase. In addition, a substance bound to a secondary antibody to be labeled is not limited to an enzyme, and may be a radioactive isotope, a fluorescent substance, a magnetic material, or colloid depending on an assay method.

In an embodiment of the present invention, when sandwich ELISA with an antibody of the present invention is carried out, a kit for sandwich ELISA can be used.

When an assay of the present invention is carried out with sandwich ELISA, for example, IgG4 can be assayed with a kit for immunoassay of IgG4, comprising: i) a solid support, ii) an antibody of the present invention, iii) a labeled different antibody against the IgG4, and iv) a component for detecting the label.

The component for detecting the label refers to a component for assaying a labeled antibody. In a case where the label is biotin, it may comprise peroxidase-labeled streptavidin, a peroxidase enzyme substrate of tetramethylbenzidine, and hydrogen peroxide. In a case where the label is alkaline phosphatase, it may comprise p-nitrophenyl phosphate. The kit may also include a washing solution, if appropriate.

In the present invention, when the kit is used, the kit preferably comprised a washing solution for removing components un-adsorbed on the solid support after IgG4 in a specimen is bound to an antibody. An example of the washing solution can include a Tris buffer solution containing a surfactant. In addition, a kit of the present invention can further comprise a specimen dilution solution, if appropriate. The specimen dilution solution for example includes a buffer solution such as Tris and the like. Such a buffer solution may contain a chelating agent such as EDTA·2Na and a mineral salt such as sodium chloride, if appropriate.

Such a detection by the immunohistochemical staining method can be carried out using a kit comprising, as components, i) a monoclonal antibody of the present invention, ii) a secondary labeled antibody, and iii) a coloring reagent. Examples of the secondary labeled antibody include an animal-derived anti-IgG antiserum and an anti-IgG polyclonal antibody which are labeled with an enzyme such as peroxidase and alkaline phosphatase. The coloring reagent includes a reagent such as a chromogenic substrate usually used for coloring an enzyme used as a label.

In the present invention, in a case where the chemiluminescent enzyme immunoassay method (CLEIA method), the fluorescent immunoassay method (FIA method), or the latex agglutination method is carried out with an antibody of the present invention, the method can be performed with a known kit for the chemiluminescent enzyme immunoassay method (CLEIA method), a known kit for the fluorescent immunoassay method (FIA method), or a known kit for the latex agglutination method.

EXAMPLES

Hereinafter, the present invention will be described in more detail with reference to Examples, Comparative Examples, and Reference Examples, but the present invention is not limited to these Examples.

<Example 1> Production and Evaluation of Monoclonal Antibody (1) Selection and Preparation of Antigen for Producing Monoclonal Antibody A hybridoma for producing a monoclonal antibody that recognizes human IgG4 was produced in accordance with the known method (for example, Kohler and Milstein, Nature (1975) 256, p. 495-497). IgG4 used as an antigen was prepared from a human serum. Specifically, a human serum is fractionated and dialyzed by ammonium sulfate precipitation, and an IgG4 antigen was then purified according to the attachment to CaptureSelectIgG4 Affinity Matrix (Thermo Fisher Scientific).

(2) Immunity 0.5 mg/mL of the human IgG4 purified by the above method from human serum was mixed with Freund's complete adjuvant (Sigma-Aldrich Co. LLC) in the same volume until they become emulsified, thereby preparing an emulsified suspension. Balb/c mouse aged 4-weeks was anesthetized with diethyl ether, and the emulsified suspension was intraperitoneally administered in an amount of 50 µg in terms of human IgG4 per mouse. An emulsified suspension prepared with Freund's incomplete adjuvant (Sigma-Aldrich Co. LLC) in the above-described manner was injected to each mouse 6 times at intervals of about two weeks. After about three weeks from sixth injection, the emulsified suspension was injected as a final immunity in the above-described manner.

(3) Establishment of Hybridoma 3 days after the final immunity, the spleen surgically extracted from each mouse under diethyl ether anesthesia was aseptically dispersed to prepare spleen cells. The cell fusion was carried out using polyethylene glycol at a 5:1 fusion ratio of the number of spleen cells to the number of myeloma cells P3-X63-Ag8-U1 (P3U1). The fused cells were dispersed in a 10% FBS (HyClone Laboratories Inc.) ASF (Cosmo Bio Co., Ltd.) HAT (Cosmo Bio Co., Ltd.) medium, and the medium was dispensed into a 48-well plate (Sumitomo Bakelite Company Limited) and cultured under conditions of 37° C. and 5% $CO_2$. 4481 hybridoma colonies were used for the following screening.

(4) Screening

The obtained hybridomas was subjected to screening of three stages to confirm 1) binding ability to IgG4, 2) specificity, and 3) adaptability to an immunological agglutination inhibition method.

1) Evaluation of Binding Ability to IgG4

The purified human IgG4 used as the antigen was dispensed into a 96-well plate (Nunc) at 0.1 µg/well. The plate was shaken by a shaker under the condition of 700 rpm and 25.0° C. for 1 hour. The solution was discarded, the plate was cleaned with 300 µL of PBST (10 mM of sodium dihydrogen phosphate; 150 mM sodium chloride; and 0.05% polyoxyethylene (20) sorbitan monolaurate; pH 7.4) 3 times, 100 µL of a blocking buffer solution (10 mM of sodium dihydrogen phosphate; 150 mM sodium chloride; and 1% block ace powder (Sumitomo Dainippon Pharma Co., Ltd.); pH 7.4) was added to each well, and then the plate was stored at 4° C. one night or more. Similarly, after cleaning with PBST, the supernatant of the culture medium for the hybridoma colony was added to each well by 100 µL, and the plate was shaken under the same condition as mentioned above. Similarly, after cleaning with PBST, a HRP labeled anti-mouse IgG(H+L) antibody (Life Technologies Corporation) diluted 10000-fold with an antibody dilute buffer solution (10 mM of sodium dihydrogen phosphate; 150 mM sodium chloride; and 0.05% polyoxyethylene (20) sorbitan monolaurate; and 0.05% bovine serum albumin; pH 7.4) was added to each well by 100 µL, and the plate was shaken under the same condition as mentioned above. Similarly, after cleaning with PBST, 100 µL of SureBlue (KPL) was added. After the plate was left at room temperature for 15 minutes, 100 µL of 0.5 mol/L sulfuric acid (Wako Pure Chemical Corporation) was added. Absorbance at a wavelength of 450 nm was measured with a microplate reader (BIO-RAD Laboratories, Inc.). Binding ability to IgG4 was observed in 192 wells among 4481 wells in total, which were selected. The selected hybridomas were monoclonized, and the culture was continued.

2) Evaluation of Specificity

Specificity of the antibody produced from the clone selected in 1) was evaluated. Myeloma human IgG1 (EMD Millipore), Myeloma human IgG2 (EMD Millipore), Myeloma human IgG3 (Sigma-Aldrich Co. LLC), Myeloma human IgG4 (EMD Millipore) were adjusted to 1 µg/mL with PBS(–). The adjusted samples were added to a 96-well plate (Thermo Fisher Scientific) by 100 µL, respectively. Shaking by a shaker as well as the procedures thereafter was carried out in the same manner as mentioned in 1). Among 192 clones, 8 clones strongly reacted to Myeloma human IgG4 as compared to Myeloma human IgG1, 2, and 3 were selected.

3) Evaluation of Adaptability to Immunological Particle Agglutination Inhibition Method Antibodies produced from the clones selected in 2) were evaluated in terms of adaptability to an immunological particle agglutination inhibition method.

i) Preparation of First Reagent (R1)

A solution containing each of antibodies derived from the selected 8 clones was added to a 2-[4-(2-hydroxyethyl)-1-piperazinyl]ethanesulfonic acid (HEPES) buffer solution 1 in a concentration of 15 µg/mL to prepare a first reagent.

ii) Preparation of Second Reagent (R2)

To 18 mL of a solution of latex particles made of polystyrene (concentration: 2%, particle size: 107 nm), 18 mL of 0.35 mg/mL human IgG4 solution roughly purified by an ordinary method from a human serum was added, and stirring was performed at room temperature for 1 hour to physically adsorb the human IgG4 onto the latex particles. Subsequently, centrifugation was carried out at 20,000 rpm for 90 minutes, and then a precipitate was recovered by discarding the supernatant. To the precipitate, 24 mL of a coating buffer solution containing 3% bovine serum albumin was added to suspend the precipitate, the resultant was completely dispersed by ultrasonication, and then stirred at room temperature for 1 hour. To the precipitate again obtained by carrying out centrifugation, 12 mL of the HEPES buffer solution 2 was added to suspend the precipitate, the resultant was completely dispersed by ultrasonication, and the concentration of latex was then adjusted to 0.12% by the HEPES buffer solution 2 to obtain a human IgG4 sensitive latex particle suspension. The human IgG4 sensitive latex particle suspension was used as a second reagent common to each first reagent.

The composition of each reagent is as follows.

HEPES Buffer Solution 1

25 mM of 2-[4-(2-hydroxyethyl)-1-piperazinyl]ethanesulfonic acid (Saikyo Kasei K.K.); 100 mM of 3-(cyclohexylamino)-1-propane sulfonic acid (Saikyo Kasei K.K.); 150 mM of sodium chloride (Wako Pure Chemical Corporation); 1 mM of EDTA.2Na (Wako Pure Chemical Corporation); 3.3% dextran 70 (Tokyo Chemical Industry Co., Ltd.); 0.1% Block-Ace (Sumitomo Dainippon Pharma Co., Ltd.); and 0.09% sodium azide (Wako Pure Chemical Corporation); pH 7.40

Coating Buffer Solution 25 mM of 2-[4-(2-hydroxyethyl)-1-piperazinyl]ethanesulfonic acid (Saikyo Kasei K.K.); 150 mM of sodium chloride (Wako Pure Chemical Corporation); 1 mM of EDTA.2Na (Wako Pure Chemical Corporation); 3% bovine serum albumin (Millipore Corporation); and 0.09% sodium azide (Wako Pure Chemical Corporation); pH 7.50

HEPES Buffer Solution 2

500 mM of 2-[4-(2-hydroxyethyl)-1-piperazinyl]ethanesulfonic acid (Saikyo Kasei K.K.); 25 mM of 2-morpholinoethanesulfonic acid (Wako Pure Chemical Corporation); 1 mM of EDTA.2Na (Wako Pure Chemical Corporation); 150 mM of L-arginine hydrochloride (Wako Pure Chemical Corporation); and 0.075% ProClin 950 (Sigma-Aldrich Co. LLC); pH 6.00 iii) Measurement of Change Amount of Absorbance

As standard samples, standard human serums with human IgG4 concentrations adjusted to 0.0, 1.6, 6.3, 12.5, 25.0, and 50.0 mg/dL were used. In addition, a saline solution was used as a sample with 0.0 mg/dL. Hitachi type 7180 automatic analyzer was used, 120 µL of the first reagent and 120 µL of the second reagent were reacted with 3 µL of a sample, and change amount of absorbance in the range of photometric points of 18 to 28 (corresponding to 1 minute to 4 minutes after addition of R2) was measured at a main wavelength of 570 nm and a complementary wavelength of 800 nm by a two-point end method (n=2). The antibodies produced by 5 clones among the 8 clones exhibited the greatest absorbance change amount at 0.0 mg/dL, and the absorbance change amount was decreased as the human IgG4 concentration was increased. Accordingly, the 5 clones (MaI4-09, MaI4-08, MaI4-01, MaI4-06, and MaI4-03) had adaptability to the immunological agglutination inhibition method. On the other hand, in the other 3 clones (MaI4-02, MaI4-04, and MaI4-05), the greatest absorbance change amount at 0.0 mg/dL, or decrease in absorbance change amount dependent on increase in human IgG4 concentration was not observed, and the other 3 clones had no adaptability to the immunological agglutination inhibition method (FIG. 1). Among the 5 clones that produce an antibody having adaptability to the immunological agglutination inhibition method, the top two clones that produce an antibody having a high absorbance change amount at 0.0 mg/dL were selected and used for the following analysis.

(5) Deposit

The selected hybridomas MaI4-08 and MaI4-09 were received by the Patent Microorganisms Depositary in the National Institute of Technology and Evaluation with NITE Receipt Nos. NITE AP-02112 (MaI4-08) and NITE AP-02113 (MaI4-09) on Sep. 1, 2015, and confirmed to be viable on Sep. 14, 2015. Thereafter, Accession Nos. NITE P-02112 (MaI4-08) and NITE P-02113 (MaI4-09) were given (accession receipt was issued on Sep. 30, 2015).

The deposit is specified by the following descriptions.

[1] Name and address of the depository

Name: National Institute of Technology and Evaluation, Patent Microorganisms Depositary Address: 2-5-8 Kazusa Kamatari Kisarazu-shi, Chiba, Japan (zip code 292-0818)

[2] Deposit date: Sep. 1, 2015

[3] Accession number

NITE P-02112 (Hybridoma MaI4-08)

NITE P-02113 (Hybridoma MaI4-09)

Thereafter, for the international deposit of the same hybridoma, a Request for transfer of microorganisms was filed with the Patent Microorganism Depositary of the National Institute of Technology and Evaluation, and NITE Receipt Nos. NITE ABP-02112 (MaI4-08) and NITE ABP-02113 (MaI4-09) were received on Jun. 8, 2018.

(6) Production of Monoclonal Antibodies by Cell Culture Method

A method for producing antibodies with the hybridomas was carried out based on a known method (for example, Monoclonal antibody: Biochemistry experimental method, Tokyo Kagaku Dojin Co. Ltd., Japan). Specifically, in order to produce a monoclonal antibody, culture in virto and culture in vivo may be used. In the in virto culture method, a hybridoma is cultured in a culture medium, and in the in vivo culture method, mouse ascites is prepared. In virto culture was selected, and supernatants of culture mediums containing monoclonal antibodies were obtained.

(7) Purification of Monoclonal Antibodies

A method for purifying the monoclonal antibodies was carried out based on a known method (for example, Monoclonal antibody: Biochemistry experimental method, Tokyo Kagaku Dojin Co. Ltd., Japan). Affinity chromatography purification is generally used for purifying a monoclonal antibody, and a sepharose column on which protein G, protein A, or the like is carried is used. A protein G sepharose column (GE Healthcare) on which protein G is carried was selected to carry out the purification. Regarding the obtained monoclonal antibodies, absorbance at 280 nm was measured to observe the antibody concentration. The concentration was adjusted, and the monoclonal antibodies were then sterilized by filtration with a filter of 0.45 μm or less.

(8) Observation of Antibodies

Isotypes of MaI4-08 and MaI4-09-produced antibodies were determined according to the attachment to Iso-Gold Rapid Mouse-Monoclonal Isotyping Kit (with κ and λ) (BioAssay Works). The isotypes were shown in Table 1.

TABLE 1

| Hybridoma identification | Heavy chain | Light chain |
|---|---|---|
| MaI4-08 | IgG1 | κ |
| MaI4-09 | IgG1 | κ |

(9) Evaluation of Specificity by ELISA

Figure 3:
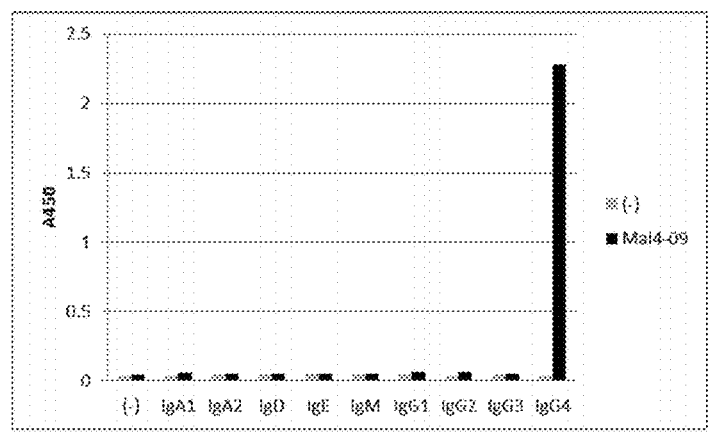
FIG. 3 shows the results of evaluating specificity of a MaI4-09-produced antibody by ELISA.
Figure 4:
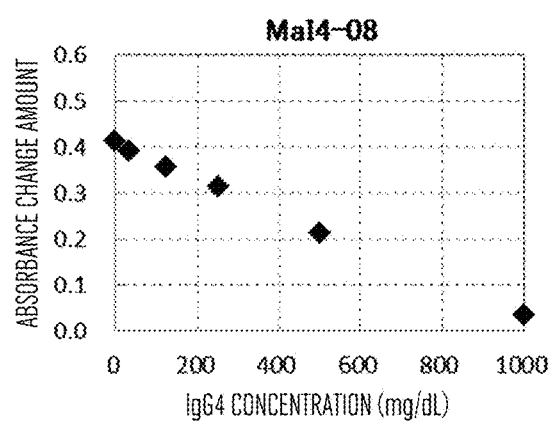
FIG. 4 shows the results of measuring change amount of absorbance with a MaI4-08-produced antibody.
Figure 5:
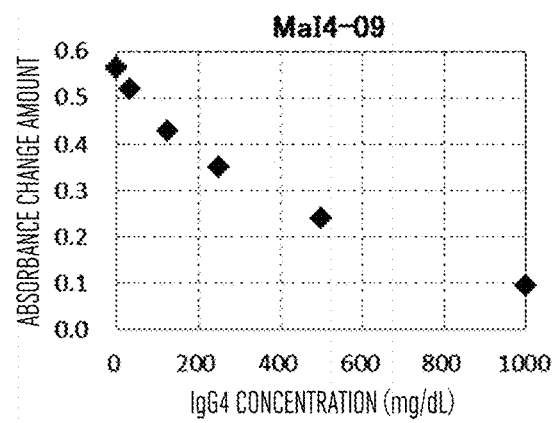
FIG. 5 shows the results of measuring change amount of absorbance with a MaI4-09-produced antibody.
Figure 6:
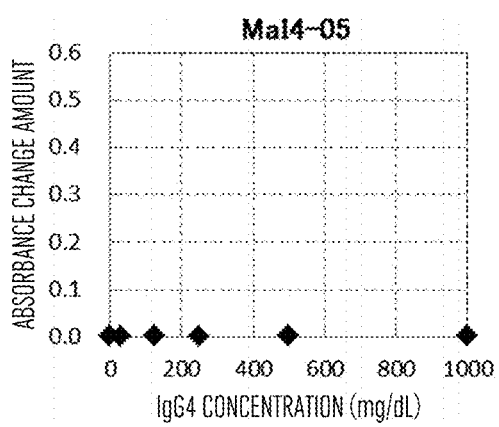
FIG. 6 shows the results of measuring change amount of absorbance with a MaI4-05-produced antibody (Comparative Example).
Figure 7:
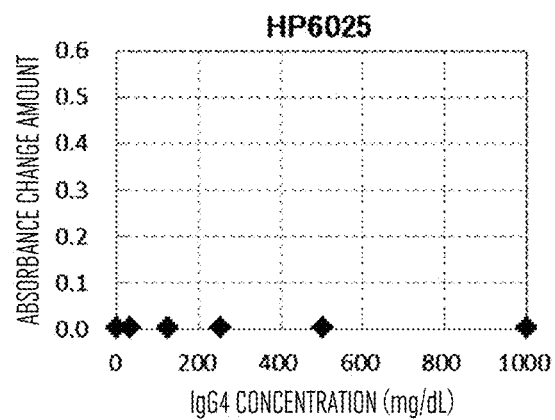
FIG. 7 shows the results of measuring change amount of absorbance with HP6025 (Comparative Example).

Myeloma human IgA1 (Abcam), Myeloma human IgA2 (Abcam), Myeloma human IgD (Abcam), Myeloma human IgE (Abcam), Myeloma human IgM (Abcam), Myeloma human IgG1 (EMD Millipore), Myeloma human IgG2 (EMD Millipore), Myeloma human IgG3 (Sigma-Aldrich Co. LLC), and Myeloma human IgG4 (EMD Millipore) were adjusted to 1 μg/mL with PBS(-). The adjusted samples were added to a 96-well plate (Thermo Fisher Scientific) by 100 μL, respectively. The plate was shaken by a shaker under the condition of 700 rpm and 25.0° C. for 1 hour. The solutions were discarded, the plate was cleaned with 300 μL of PBST 3 times, 100 μL of a blocking buffer solution was added to each well, and then the plate was stored at 4° C. one night or more. Similarly, after cleaning with PBST, the MaI4-08 and MaI4-09-produced antibodies were adjusted to 1 μg/mL with an antibody dilute buffer solution and then added to each well by 100 μL, and the plate was shaken under the same condition as mentioned above. Similarly, after cleaning with PBST, a HRP labeled anti-mouse IgG antibody (Abcam) diluted 4000-fold with an antibody dilute buffer solution was added to each well by 100 μL, and the plate was shaken under the same condition as mentioned above. Similarly, after cleaning with PBST, 100 μL of SureBlue (KPL) was added. 5 or 3 minutes later, 100 μL of 0.5 mol/L sulfuric acid (Wako Pure Chemical Corporation) was added to each of MaI4-08 and MaI4-09. Absorbance at a wavelength of 450 nm was measured with a microplate reader (BIO-RAD Laboratories, Inc.). As a result, a strong signal was given to Myeloma human IgG4 as compared to the other samples (Tables 2 and 3, and FIGS. 2 and 3).

TABLE 2

|  | (-) | IgA1 | IgA2 | IgD | IgE | IgM | IgG1 | IgG2 | IgG3 | IgG4 |
|---|---|---|---|---|---|---|---|---|---|---|
| (-) | 0.058 | 0.052 | 0.051 | 0.055 | 0.052 | 0.053 | 0.049 | 0.045 | 0.048 | 0.050 |
| MaI4-08 | 0.042 | 0.043 | 0.043 | 0.042 | 0.041 | 0.042 | 0.048 | 0.047 | 0.044 | 2.044 |

TABLE 3

|  | (-) | IgA1 | IgA2 | IgD | IgE | IgM | IgG1 | IgG2 | IgG3 | IgG4 |
|---|---|---|---|---|---|---|---|---|---|---|
| (-) | 0.040 | 0.041 | 0.043 | 0.047 | 0.049 | 0.044 | 0.046 | 0.042 | 0.045 | 0.041 |
| MaI4-09 | 0.048 | 0.058 | 0.050 | 0.051 | 0.050 | 0.055 | 0.063 | 0.064 | 0.052 | 2.284 |

(10) Amino Acid Sequence Analysis of Monoclonal Antibody

MaI4-08 and MaI4-09 each were subjected to mRNA extraction, cloning, and sequencing according to the protocol of Fusion Antibodies Ltd. As a result of analysis, variable regions of MaI4-08 were SEQ ID NO: 5 (heavy chain variable region) and SEQ ID NO: 6 (light chain variable region), variable regions of MaI4-09 were SEQ ID NO: 7 (heavy chain variable region) and SEQ ID NO: 8 (light chain variable region). The amino acid sequences of CDRs were as shown in Table 4.

TABLE 4

|  |  | CDR1 | CDR2 | CDR3 |
|---|---|---|---|---|
| MaI4-08 | Heavy chain | SYILH (SEQ ID NO: 9) | YINPYNDGTKYKEKFKG (SEQ ID NO: 10) | SGGGYGNYAWFAY (SEQ ID NO: 11) |
|  | Light chain | RASQDIGSSLN (SEQ ID NO: 12) | ATSSLDS (SEQ ID NO: 13) | LQYASYPPT (SEQ ID NO: 14) |
| MaI4-09 | Heavy chain | SSVMH (SEQ ID NO: 15) | YINPYNDGTRYNEKFQG (SEQ ID NO: 16) | SFYYGNSHVLFAY (SEQ ID NO: 17) |
|  | Light chain | KASQDINSYLS (SEQ ID NO: 18) | RANRLVD (SEQ ID NO: 19) | LQYDELPYT (SEQ ID NO: 20) |

<Example 2> Assay Reagent Preparation and Assay with MaI4-08 and MaI4-09-Produced Antibodies (1) Preparation of Reagents 1) Preparation of First Reagent (R1)

A MaI4-08 or MaI4-09-produced antibody solution was added to a 2-[4-(2-hydroxyethyl)-1-piperazinyl]ethanesulfonic acid (HEPES) buffer solution 1 in a concentration of 15 μg/mL to prepare a first reagent. Similarly, as control reagents, a MaI4-05-produced antibody and a commercially available antibody HP6025 (Millipore Corporation) were added to a HEPES buffer solution 1 to prepare solutions.

2) Preparation of Second Reagent (R2)

To 18 mL of a solution of latex particles made of polystyrene (concentration: 2%, particle size: 107 nm), 18 mL of 0.35 mg/mL human IgG4 solution roughly purified by a general method from a human serum was added, and stirring was performed at room temperature for 1 hour to physically adsorb the human IgG4 onto the latex particles. Subsequently, centrifugation was carried out at 20,000 rpm for 90 minutes, and then a precipitate was recovered by discarding the supernatant. To the precipitate, 24 mL of coating buffer solution containing 3% bovine serum albumin was added to suspend the precipitate, the resultant was completely dispersed by ultrasonication, and then stirred at room temperature for 1 hour. To the precipitate again obtained by carrying out centrifugation, 12 mL of the HEPES buffer solution 2 was added to suspend the precipitate, the resultant was completely dispersed by ultrasonication, and the concentration of latex was then adjusted to 0.12% by the HEPES buffer solution 2 to obtain a human IgG4 sensitive latex particle suspension. The human IgG4 sensitive latex particle suspension was used as a second reagent common to each first reagent.

The composition of each reagent is as follows.

TABLE 5

| HEPES buffer solution 1 | | |
|---|---|---|
| 2-[4-(2-Hydroxyethyl)-1-piperazinyl]ethanesulfonic acid | Saikyo Kasei K.K. | 25 mM |
| 3-(Cyelohexylamino)-1-propane sulfonic acid | Saikyo Kasei K.K. | 100 mM |
| Sodium chloride | Wake Pure Chemical Corporation | 150 mM |
| EDTA · 2Na | Wake Pure Chemical Corporation | 1 mM |
| Dextran 70 | Tokyo Chemical Industry Co., Ltd. | 3.3% |
| Block-Ace | Sumitomo Dainippon Pharma Co., Ltd. | 0.1% |
| Sodium azide | Wako Pure Chemical Corporation | 0.09% |
| pH7.40 | | |

TABLE 6

| Coating buffer solution | | |
|---|---|---|
| 2-[4-(2-Hydroxyethyl)-1-piperazinyl]ethanesulfonic acid | Saikyo Kasei K.K. | 25 mM |
| Sodium chloride | Wako Pure Chemical Corporation | 150 mM |
| EDTA · 2Na | Wako Pure Chemical Corporation | 1 mM |
| Bovine serum albumin | Millipore Corporation | 3% |
| Sodium azide | Wako Pure Chemical Corporation | 0.09% |
| pH7.50 | | |

TABLE 7

| HEPES buffer solution 2 | | |
|---|---|---|
| 2-[4-(2-Hydroxyethyl)-1-piperazinyl]ethanesulfonic acid | Saikyo Kasei K.K. | 500 mM |
| 2-Morpholinoethanesulfonic acid | Wako Pure Chemical Corporation | 25 mM |
| EDTA · 2Na | Wako Pure Chemical Corporation | 1 mM |
| L-Arginine hydrochloride | Wako Pure Chemical Corporation | 150 mM |
| ProClin 950 | Sigma-Aldrich Co. LLC | 0.075% |
| pH6.00 | | |

(2) Measurement of Change Amount of Absorbance

Standard human serums with human IgG4 concentrations adjusted to 1.6, 6.3, 12.5, 25, and 50 mg/dL were used as standard samples. In the assay, specimen samples were diluted 20-fold and then assayed, and the final standard sample concentrations are therefore set to 20-fold higher ones, namely 31.3, 125, 250, 500, and 1000 mg/dL. The final concentrations of all samples described later are set to 20-fold higher ones. A saline solution containing 0.85% sodium chloride was used as a sample with a human IgG4 concentration of 0.0 mg/dL. For the measurement of human IgG4 concentrations, Hitachi type 7180 automatic analyzer was used, 120 μL of the first reagent and 120 μL of the second reagent were reacted with 3 μL of a sample, and change amounts of absorbance in the range of photometric points of 18 to 28 (corresponding to 1 minute to 4 minutes after addition of R2) were measured at a main wavelength of 570 nm and a complementary wavelength of 800 nm by a two-point end method (n=2).

(3) Measurement Result

Upon the measurement of the human IgG4 concentrations with the above-mentioned reagents, change amounts of absorbance are shown in Table 8 and FIGS. 4, 5, 6, and 7.

TABLE 8

| Human IgG4 concentration | Absorbance change amount in 800 nm | | | |
|---|---|---|---|---|
| (mg/dL) | MaI4-08 | MaI4-09 | MaI4-05 | HP6025 |
| 0.0 | 0.4123 | 0.5648 | 0.0029 | 0.0030 |
| 31.3 | 0.3928 | 0.5193 | 0.0027 | 0.0036 |
| 125 | 0.3557 | 0.4305 | 0.0024 | 0.0033 |
| 250 | 0.3144 | 0.3519 | 0.0021 | 0.0034 |
| 500 | 0.2151 | 0.2414 | 0.0021 | 0.0031 |
| 1000 | 0.0350 | 0.0955 | 0.0016 | 0.0030 |

As demonstrated in Table 8 and FIGS. 4 to 7, in a case where the MaI4-08-produced antibody or the MaI4-09-produced antibody was used as an anti-human IgG4 mouse monoclonal antibody in the first reagent, change amount of absorbance was decreased as the human IgG4 concentration was increased. On the other hand, in a case where the control reagent prepared by the MaI4-05-produced antibody or the commercially available antibody HP6025 was used, change in absorbance dependent on human IgG4 concentrations was not observed. Therefore, it was found that it is difficult to apply a reagent prepared by the MaI4-05-produced antibody and the commercially available antibody HP6025 to a latex (particle) agglutination inhibition method with an automatic analyzer. On the other hand, it was found that the reagents prepared by the MaI4-08 and MaI4-09-produced antibodies can be applied to a latex (particle) agglutination inhibition method, and are useful to measure a human IgG4 concentration with an automatic analyzer.

(4) Evaluation of Dilution Linearity

In a case where the MaI4-08-produced antibody or the MaI4-09-produced antibody was used as an anti-human IgG4 mouse monoclonal antibody in the first reagent, dilution linearity was evaluated. A standard human serum with a human IgG4 concentration adjusted to 1000 mg/dL, and specimen samples serially diluted with a saline solution containing 0.85% sodium chloride were used as samples. A saline solution was used for a sample having a human IgG4 concentration of 0.0 mg/dL. For the measurement of the human IgG4 concentration, 120 μL of the first reagent and 120 μL of the second reagent were reacted with 3 μL of a sample using Hitachi type 7180 automatic analyzer, and change amount of absorbance in the range of photometric points of 18 to 28 (corresponding to 1 minute to 4 minutes after addition of R2) was measured at a main wavelength of 570 nm and a complementary wavelength of 800 nm by a two-point end method (n=2). A calibration curve was created from the results of Table 8, and the human IgG4 concentration in a sample was calculated therefrom.

(5) Evaluation of Tolerance to Prozone Phenomenon

In a case where the MaI4-08-produced antibody or the MaI4-09-produced antibody was used as an anti-human IgG4 mouse monoclonal antibody in the first reagent, tolerance to a prozone phenomenon was evaluated. A standard human serum with a human IgG4 concentration adjusted to 8000 mg/dL and specimen samples serially diluted with a saline solution containing 0.85% sodium chloride were used as samples. For the measurement of human IgG4 concentrations, 120 μL of the first reagent and 120 uL of the second reagent were reacted with 3 uL of a sample using Hitachi type 7180 automatic analyzer, and change amount of absorbance in the range of photometric points of 18 to 28 (corresponding to 1 minute to 4 minutes after addition of R2) was measured at a main wavelength of 570 nm and a complementary wavelength of 800 nm by a two-point end method (n=2). A calibration curve was created from the results of Table 8, and the human IgG4 concentration in a sample was calculated therefrom.

(6) Evaluation of Specificity to Human IgG4

In a case where the MaI4-08-produced antibody or the MaI4-09-produced antibody was used as an anti-human IgG4 mouse monoclonal antibody in the first reagent, specificity to human IgG4 was evaluated. As a sample, Myeloma human IgG4 solution (EMD Millipore) adjusted to 3000 mg/dL was used. In addition, as control samples, Myeloma human IgG1 solution (EMD Millipore), Myeloma human IgG2 solution (EMD Millipore), and Myeloma human IgG3 solution (Sigma-Aldrich Co. LLC) prepared similarly to the above were used. A saline solution was used as a blank sample. For the measurement of human IgG4 concentrations, 120 μL of the first reagent and 120 μL of the second reagent were reacted with 3 μL of a sample using Hitachi type 7180 automatic analyzer, and change amount of absorbance in the range of photometric points of 18 to 28 (corresponding to 1 minute to 4 minutes after addition of R2) was measured at a main wavelength of 570 nm and a complementary wavelength of 800 nm by a two-point end method (n=2). A calibration curve was created from the results of Table 8 and the human IgG4 concentration in a sample was calculated therefrom.

(7) Assay Results

The results are shown in FIGS. 8 to 13 and Tables 9 and 10.

TABLE 9

| | MaI4-08 | | | | |
|---|---|---|---|---|---|
| Sample | Blank | IgG1 | IgG2 | IgG3 | IgG4 |
| Measured value | 0.0 | 10.1 | 12.8 | 4.1 | 1088.8 |

TABLE 10

| | MaI4-09 | | | | |
|---|---|---|---|---|---|
| Sample | Blank | IgG1 | IgG2 | IgG3 | IgG4 |
| Measured value | 0.0 | 9.5 | 11.8 | 4.1 | 1331.0 |

Figure 8:
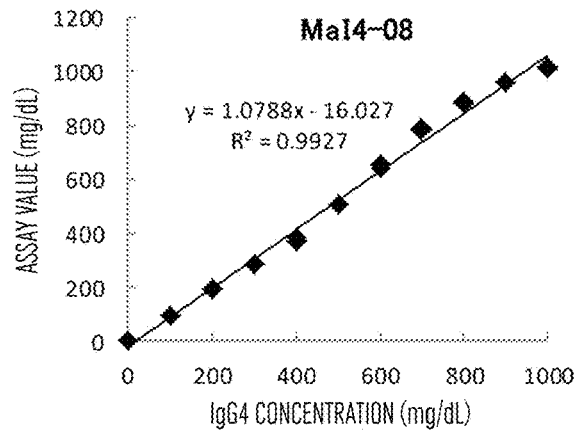
FIG. 8 shows the results of evaluating dilution linearity of a MaI4-08-produced antibody.
Figure 9:
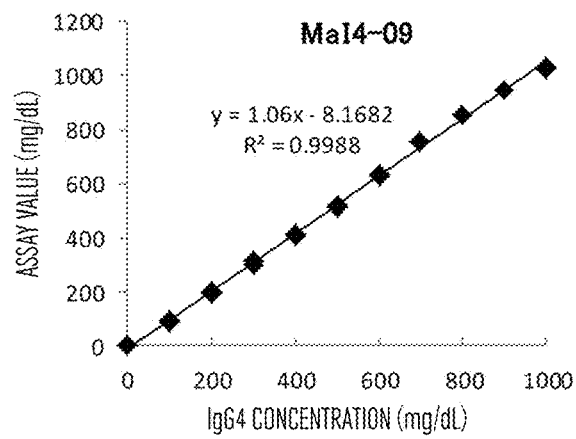
FIG. 9 shows the results of evaluating dilution linearity of a MaI4-09-produced antibody.
Figure 10:
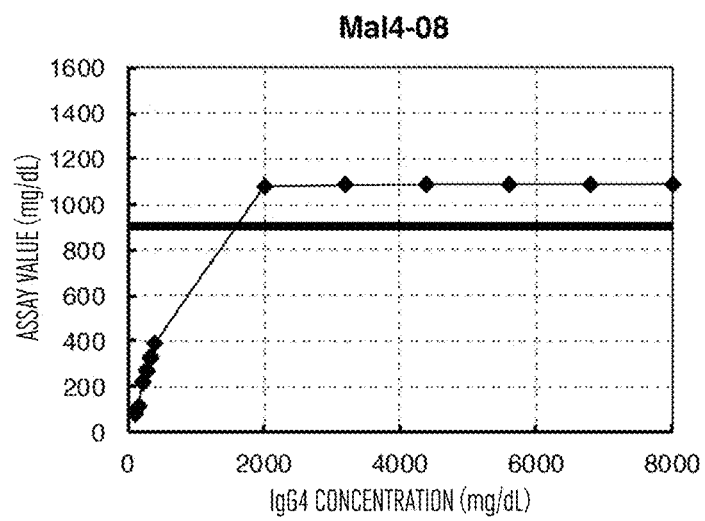
FIG. 10 shows the results of evaluating tolerance to a prozone phenomenon of a MaI4-08-produced antibody.
Figure 11:
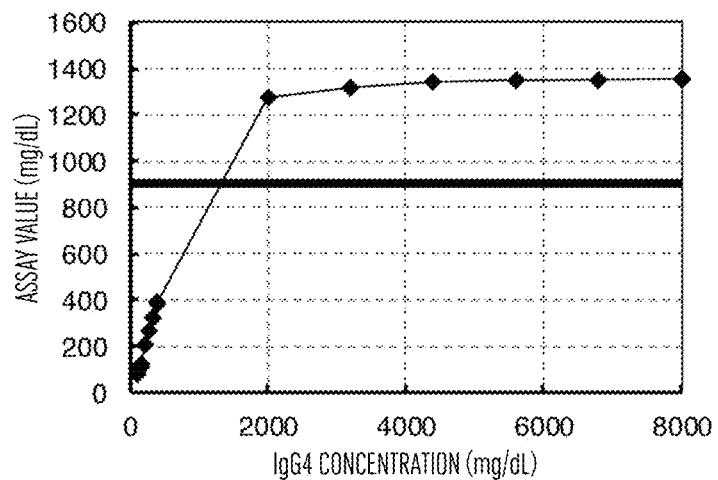
FIG. 11 shows the results of evaluating tolerance to a prozone phenomenon of a MaI4-09-produced antibody.
Figure 12:
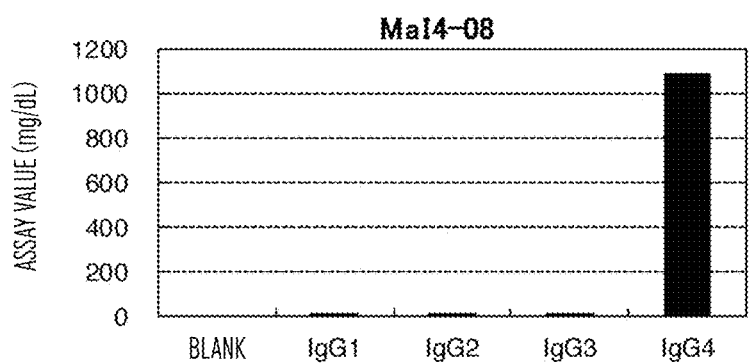
FIG. 12 shows the results of evaluating specificity of a MaI4-08-produced antibody to human IgG4.
Figure 13:
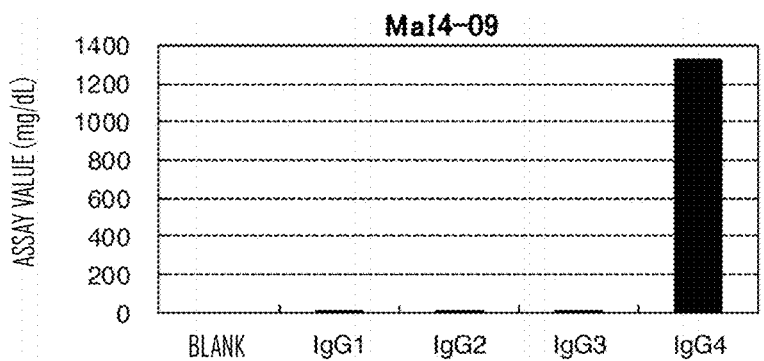
FIG. 13 shows the results of evaluating specificity of a MaI4-09-produced antibody to human IgG4.

In a case where the anti-human IgG4 mouse monoclonal antibodies produced by the hybridoma of the present invention was used in the first reagent, it was confirmed that the dilution linearity was sufficient within the calibration range of 0 to 1000 mg/dL (FIGS. 8 and 9). Regarding the prozone phenomenon, the measured values were not decreased up to 8000 mg/dL (FIGS. 10 and 11). Furthermore, reactivity to IgG1, IgG2 or IgG3 were almost not observed (FIGS. 12 and 13 and Tables 9 and 10).

As described above, it was newly found that there are antibodies that are not suitable for the immunological particle agglutination inhibition method not only in the screening stage but also in an antibody (HP6025) reported as an anti-IgG4 monoclonal antibody (Non-Patent Literature 6). In order to clarify difference between an antibody suitable for the immunological particle agglutination inhibition method and an antibody not suitable for the immunological particle agglutination inhibition method, interaction analysis and epitope analysis of the antibodies were carried out.

<Example 3> Interaction Analysis

MaI4-08 and MaI4-09-produced antibodies, and, as a control, MaI4-05-produced antibody and 1 mg/mL of HP6025 were adjusted to 1 mg/mL. In addition, 1 mg/mL of IgG4 was prepared from the one purified from human serum. According to the protocol of Sumika Chemical Analysis Service, Ltd., IgG4 was immobilized onto a chip by an amino coupling method, and a sensorgram was obtained by a Biacore model. The obtained binding rate constant ($k_a$), dissociation rate constant ($k_d$), and dissociation constant (KD) were as shown in Table 11.

TABLE 11

| | $k_a[M^{-1}S^{-1}]$ | $k_d[S^{-1}]$ | KD[M] |
|---|---|---|---|
| MaI4-08 | 5.492E+05 | 2.229E−04 | 4.058E−10 |
| MaI4-09 | 4.419E+05 | 1.444E−04 | 3.268E−10 |
| MaI4-05 | 2.858E+04 | 6.492E−05 | 2.272E−09 |
| HP6025 | 1.669E+03 | 6.814E−04 | 4.084E−07 |

Among 3 types of antibodies, the binding rate constant $k_a$ of the MaI4-05-produced antibody was one-tenth or less of those of the MaI4-08 and MaI4-09-produced antibodies. The binding rate constant $k_a$ of the HP6025 antibody was one-hundredth or less of those of the MaI4-08 and MaI4-09-produced antibodies.

<Example 4> Analysis of Epitope

From Uniprot, an amino acid sequence of the human IgG4 heavy chain constant region was obtained (P01861, SEQ ID NO: 4). The obtained amino acid sequence was partially or not deleted to obtain the amino acid sequences H1 to 12 (FIG. 14) represented by SEQ ID NO: 4 and 25 to 35, respectively, and a GST tag was linked to a N terminal of each of the sequences to obtain a designed peptide. H1 (SEQ ID NO: 4) consists of an amino acid sequence of a full-length human IgG4 heavy chain constant region. H2 consists of the amino acid sequence at positions 1 to 274 of the human IgG4 heavy chain constant region (SEQ ID NO: 25). H3 consists of the amino acid sequence at positions 1 to 220 of the human IgG4 heavy chain constant region (SEQ ID NO: 26). H4 consists of the amino acid sequence at positions 1 to 165 of the human IgG4 heavy chain constant region (SEQ ID NO: 27). H5 consists of the amino acid sequence at positions 1 to 110 of the human IgG4 heavy chain constant region (SEQ ID NO: 28). H6 consists of the amino acid sequence at positions 1 to 55 of the human IgG4 heavy chain constant region (SEQ ID NO: 29). H7 consists of the amino acid sequence at positions 56 to 327 of the human IgG4 heavy chain constant region (SEQ ID NO: 30). H8 consists of the amino acid sequence at positions 111 to 327 of the human IgG4 heavy chain constant region (SEQ ID NO: 31). H9 consists of the amino acid sequence at positions 166 to 327 of the human IgG4 heavy chain constant region (SEQ ID NO: 32). H10 consists of the amino acid sequence at positions 221 to 327 of the human IgG4 heavy chain constant region (SEQ ID NO: 33). H11 consists of the amino acid sequence at positions 275 to 327 of the human IgG4 heavy chain constant region (SEQ ID NO: 34). H12 consists of the amino acid sequence at positions 99 to 220 of the human IgG4 heavy chain constant region (SEQ ID NO: 35).

In addition, in an amino acid sequence (H10, SEQ ID NO: 33) in the human IgG4 heavy chain CH3 region, human IgG4-specific sequences were partially substituted with corresponding amino acids of the human IgG1 heavy chain constant region to obtain the amino acid sequences H31 to 39 (FIG. 15) represented by SEQ ID NOS: 36 to 44, respectively, and a GST tag was linked to an N terminal of each of the sequences to obtain a designed peptide. H31 is based on the amino acid sequence H10 wherein an arginine residue is substituted for a glutamine residue at position 235 in the human IgG4 heavy chain constant region. See SEQ ID NO: 36. H32 is based on the amino acid sequence H10 wherein a lysine residue is substituted for an arginine residue at position 289 in the human IgG4 heavy chain constant region. See SEQ ID NO: 37. H33 is based on the amino acid sequence H10 wherein a glutamic acid residue is substituted for a glutamine residue at position 299 in the human IgG4 heavy chain constant region. See SEQ ID NO: 38. H34 is based on the amino acid sequence H10 wherein a proline residue is substituted for a leucine residue at position 325 in the human IgG4 heavy chain constant region. See SEQ ID NO: 39. H35 is based on the amino acid sequence H10 wherein, in the human IgG4 heavy chain constant region, an arginine residue is substituted for a glutamine residue at position 235; a lysin residue is substituted for an arginine residue at position 289; a glutamine residue is substituted for a glutamic acid residue at position 299; and a proline residue is substituted for a leucine residue at position 325. See SEQ ID NO: 40. H36 is an amino acid sequence of the human IgG4 heavy chain constant region wherein, for a human IgG4 specific sequence at positions of 221 to 327 of the amino acid sequence of the human IgG4 heavy chain constant region, a corresponding amino acid sequence of IgG1 is substituted. See SEQ ID NO: 41. H37 is based on the amino acid sequence H10 wherein, in the human IgG4 heavy chain constant region, a lysin residue is substituted for an arginine residue at position 289; and a proline residue substituted for a leucine residue at position 325. See SEQ ID NO: 42. H38 is based on the amino acid sequence H10 wherein, in the human IgG4 heavy chain constant region, a lysin residue is substituted for an arginine residue at position 289; glutamine is substituted for a glutamic acid residue at position 299; and a proline residue is substituted for a leucine residue at position 325. See SEQ ID NO: 43. H39 is based on the amino acid sequence H36 wherein a glutamic acid residue is substituted for a glutamine residue at position 299 in the human IgG4 heavy chain constant region. See SEQ ID NO: 44.

Based on the designed amino acid sequences, base sequences suitable for expressing protein in *E. coli* were designed according to the protocol of GenScript Corporation, thereby preparing vector pGEX-6P-1 (GE Healthcare Bio-Sciences Corp.) to which the respective base sequences are inserted. The prepared expression plasmid was introduced to *E. coli* BL 21 strain, thereby obtaining a transformant. The transformant was cultured by an ordinary method and a protein expression was induced by IPTG. After the cells were collected by centrifugation, the cells were dissolved with an ordinary lysis solution, and subjected to ultrasonication. 6 µL of an SDS sample buffer solution was added to 6 µL of the obtained lysate. The respective prepared samples were subjected to a heat treatment at 95° C. for 5 minutes. 10 µL of the *E. coli* disrupted sample was added to each well of 5 to 20% electrophoresis gel (Atto Corporation) to which an SDS electrophoresis buffer solution was added. Similarly, a molecular weight standard (Bio-Rad Laboratories, Inc.) was added to each well and electrophoresed. After completing the electrophoresis, the electrophoresis gel was transcribed to a PVDF membrane (Millipore Corporation) with a transfer buffer solution. The PVDF membrane was immersed in a membrane blocking buffer solution, and then shaking was carried out at room temperature for 30 minutes. Amino groups of MaI4-08, MaI4-09, and MaI4-05-produced antibodies were subjected to a POD labeling treatment with a POD labeling kit (Dojindo Molecular Technologies, Inc.). The obtained labeled antibodies each were diluted 1000-fold by PBST. After the PVDF membrane was cleaned with PBST, the antibody solutions prepared each were added to the PVDF membrane, and then the reaction was performed at room temperature for 1 hour. After the PVDF membrane was cleaned by PBST, a signal was detected with ECL Prime Western Blotting Detection Reagents (GE Healthcare) with Image Quant Las4000.

Figure 16:
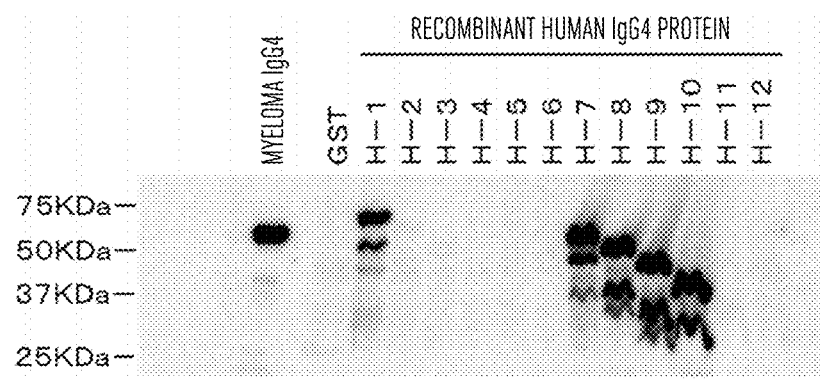
FIG. 16 shows the results of Western blot analysis of a MaI4-08-produced antibody with respect to peptides H1 to 12.
Figure 17:
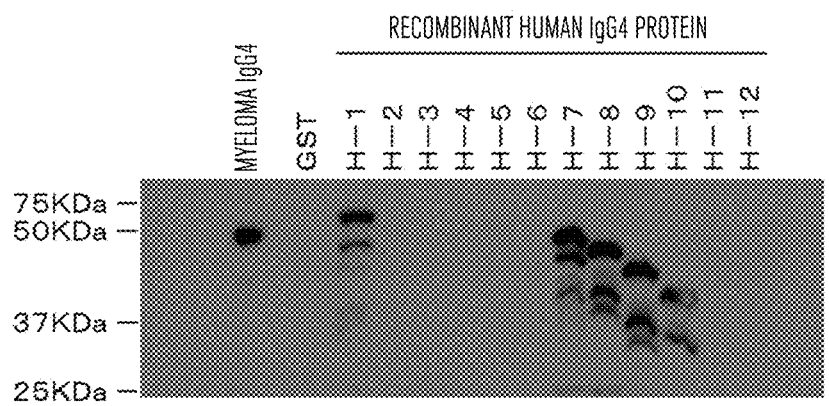
FIG. 17 shows the results of Western blot analysis of a MaI4-09-produced antibody with respect to peptides H1 to 12.

As a result, regarding both the MaI4-08 and MaI4-09-produced antibodies, signals were observed in relation to H-1, H-7, H-8, H-9, and H-10. Accordingly, it was found that the epitopes of the MaI4-08 and MaI4-09-produced antibodies are present in an amino acid sequence at positions 221 to 327 of the human IgG4 heavy chain constant region (FIGS. 16 and 17).

Figure 18:
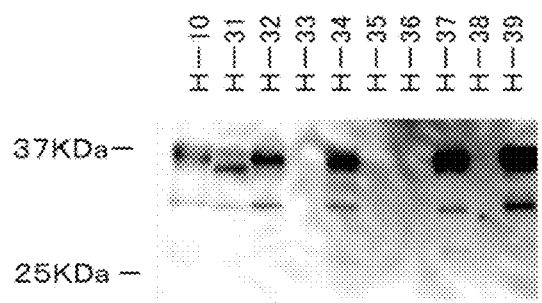
FIG. 18 shows the results of Western blot analysis of a MaI4-08-produced antibody with respect to peptides H10 and H31 to 39.
Figure 19:
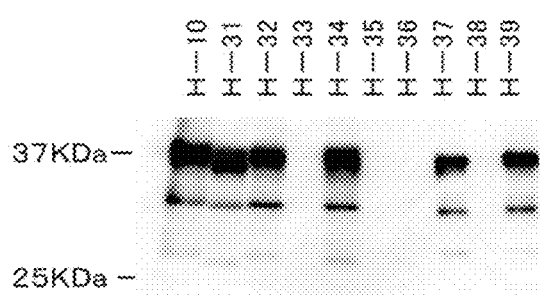
FIG. 19 shows the results of Western blot analysis of MaI4-09 with respect to peptides H10 and H31 to 39.

Regarding the MaI4-08 and MaI4-09-produced antibodies, signals were also observed under the condition in which glutamic acid was maintained at position 299 (H-10, H-31, H-32, H-34, and H-37), but signals were not observed under the condition in which glutamic acid at position 299 was substituted with glutamine (H-33, H-35, H-36, and H-38). Therefore, it was found that the epitopes of the MaI4-08 and MaI4-09-produced antibodies were present in the amino acid sequence at positions of 221 to 327 of the human IgG4 heavy chain constant region, the amino acid sequence being necessary to contain a glutamic acid residue at position 299 in the human IgG4 heavy chain constant region (FIGS. 18 and 19).

Figure 20:
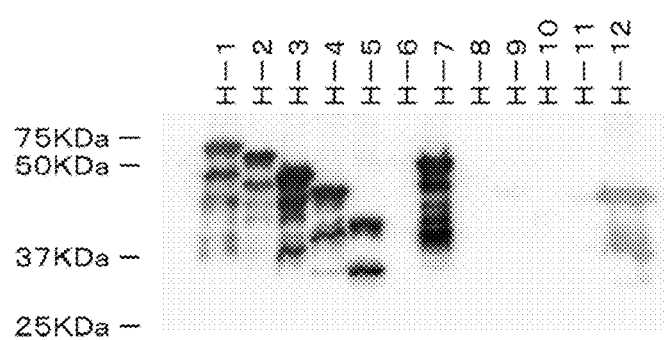
FIG. 20 shows the results of Western blot analysis of MaI4-05 with respect to peptides H1 to 12.

Meanwhile, regarding the MaI4-05-produced antibody, a signal was observed only in the amino acid sequence at positions 99 to 110, namely a sequence containing a hinge region (H-1, H-2, H-3, H-4, H-5, H-7, and H-12). Therefore, it was found that the epitope of the MaI4-05-produced antibody was present in the amino acid sequence at positions of 99 to 110 of the human IgG4 heavy chain constant region (FIG. 20).

The amino acid sequences of H-1 to H-12 and H-31 to H-39 are shown as follows.

TABLE 12-1

| Sample name | Amino acid sequence |
|---|---|
| H1<br>SEQ ID NO: 4 | ASTKGPSVFPLAPCSRSTSESTAALGCLVKDYFPEPVTVSWNSGALTSGVHTFPAVLQSSGL<br>YSLSSVVTVPSSSLGTKTYTCNVDHKPSNTKVDKRVESKYGPPCPSCPAPEFLGGPSVFLFP<br>PKPKDTLMISRTPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEEMTKNQVSLTCL<br>VKGFYPSDIAVEWESNGQPENNYKTTPPVLDSDGSFFLYSRLTVDKSRWQEGNVFSCSVMHE<br>ALHNHYTQKSLSLSLGK |
| H2<br>SEQ ID NO: 25 | ASTKGPSVFPLAPCSRSTSESTAALGCLVKDYFPEPVTVSWNSGALTSGVHTFPAVLQSSGL<br>YSLSSVVTVPSSSLGTKTYTCNVDHKPSNTKVDKRVESKYGPPCPSCPAPEFLGGPSVFLFP<br>PKPKDTLMISRTPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEEMTKNQVSLTCL<br>VKGFYPSDIAVEWESNGQPENNYKTT |
| H3<br>SEQ ID NO: 26 | ASTKGPSVFPLAPCSRSTSESTAALGCLVKDYFPEPVTVSWNSGALTSGVHTFPAVLQSSGL<br>YSLSSVVTVPSSSLGTKTYTCNVDHKPSNTKVDKRVESKYGPPCPSCPAPEFLGGPSVFLFP<br>PKPKDTLMISRTPEVTCVVVDVSQEDPEVQFNWYVDGVEVHNAKTKPREEQFNSTYRVVSVL<br>TVLHQDWLNGKEYKCKVSNKGLPSSIEKTISKAK |
| H4<br>SEQ ID NO: 27 | ASTKGPSVFPLAPCSRSTSESTAALGCLVKDYFPEPVTVSWNSGALTSGVHTFPAVLQSSGL<br>YSLSSVVTVPSSSLGTKTYTCNVDHKPSNTKVDKRVESKYGPPCPSCPAPEFLGGPSVFLFP<br>PKPKDTLMISRTPEVTCVVVDVSQEDPEVQFNWYVDGVEVH |
| H5<br>SEQ ID NO: 28 | ASTKGPSVFPLAPCSRSTSESTAALGCLVKDYFPEPVTVSWNSGALTSGVHTFPAVLQSSGL<br>YSLSSVVTVPSSSLGTKTYTCNVDHPSNTKVDKRVESKYGPPCPSCP |
| H6<br>SEQ ID NO: 29 | ASTKGPSNFPLAPCSRSTSESTAALGUNKDYFPEPVTVANSGALTSGVHTFPA |
| H7<br>SEQ ID NO: 30 | VLQSSGLYSLSSVVTVPSSSLGTKTYTCNVDHKPSNTKVDKRVESKYGPPCPSCPAPEFLGG<br>PSVFLFPPKPKDTLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYTLPPSQEEMTKN<br>QVSLTCLVKGFYPSDIAVEWESNGQPENNYKTTPPVLDSDGSFFLYSRLTVDKSRWQEGNVF<br>SCSVMHEALHNHYTQKSLSLSLGK |
| H8<br>SEQ ID NO: 31 | APEFLGGPSVFLFPPKPKDTLMISRTPEVTCVVVDVSQEDPEVQFNWYVDGVEVHNAKTKPR<br>EEQFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDKSR<br>WQEGNVFSCSVMHEALHNHYNHYTQSLSLGK |
| H9<br>SEQ ID NO: 32 | NAKTKPREEQFNSTYRVVSVLTVLHQDWLNGKEYKCKVSNKGLPSSIEKTISKAKGQPREPQ<br>VYTLPPSQEEMTKNQVSLTCLVKGFYPSDIAVEWESNGQPENNYKTTPPVLDSDGSFFLYSR<br>LTVDKSRWQEGNVFSCSVMHEALHNHYTQKSLSLSLGK |
| H10<br>SEQ ID NO: 33 | GQPREPQVYT LPPSQEEMTK NQVSLTCLVK GFYPSDIAVE WESNGQPENN<br>YKTTPPVLDSDGSFFLYSRL TVDKSRWQEG NVFSCSVMHE ALHNYTQKS LSLSLGK |

TABLE 12-2

| H11<br>SEQ ID NO: 34 | PPVLDS DGSFFLYSRL TVDKSRWQEG NVFSCSVMHE ALHNYTQKS LSLSLGK |
|---|---|
| H12<br>SEQ ID NO: 35 | ESKYGPPCPSCPAPEFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAK |
| H31<br>SEQ ID NO: 36 | GQPREPQVYT LPPSREEMTK NQVSLTCLVK GFYPSDIAVE WESNGQPENN<br>YKTTPPVLDS DGSFFLYSRL TVDKSRWQEG NVFSCSVMHE ALHNYTQKS LSLSLGK |
| H32<br>SEQ ID NO: 37 | GQPREPQVYT LPPSQEEMTK NQVSLTCLVK GFYPSDIAVE WESNGQPENN<br>YKTTPPVLDS DGSFFLYSKL TVDKSRWQEG NVFSCSVMHE ALHNYTQKS LSLSLGK |
| H33<br>SEQ ID NO: 38 | GQPREPQVYT LPPSQEEMTK NQVSLTCLVK GFYPSDIAVE WESNGQPENN<br>YKTTPPVLDS DGSFFLYSRL TVDKSRWQQG NVFSCSVMHE ALHNYTQKS LSLSLGK |

TABLE 12-2-continued

```
H34           GQPREPQVYT LPPSQEEMTK NQVSLTCLVK GFYPSDIAVE WESNGQPENN
SEQ ID NO: 39 YKTTPPVLDS DGSFFLYSRL TVDKSRWQEG NVFSCSVMHE ALHNHYTQKS LSLSPGK

H35           GQPREPQVYT LPPSREEMTK NQVSLTCLVK GFYPSDIAVE WESNGQPENN
SEQ ID NO: 40 YKTTPPVLDS DGSFFLYSKL TVDKSRWQQG NVFSCSVMHE ALHNHYTQKS LSLSPGK

H36           GQPREPQVYT LPPSRDELTK NQVSLTCLVK GFYPSDIAVE WESNGQPENN
SEQ ID NO: 41 YKTTPPVLDS DGSFFLYSKL TVDKSRWQQG NVFSCSVMHE ALHNHYTQKS LSLSPGK

H37           GQPREPQVYT LPPSQEEMTK NQVSLTCLVK GFYPSDIAVE WESNGQPENN
SEQ ID NO: 42 YKTTPPVLDS DGSFFLYSKL TVDKSRWQEG NVFSCSVMHE ALHNHYTQKS LSLSPGK

H38           GQPREPQVYT LPPSQEEMTK NQVSLTCLVK GFYPSDIAVE WESNGQPENN
SEQ ID NO: 43 YKTTPPVLDS DGSFFLYSKL TVDKSRWQQG NVFSCSVMHE ALHNHYTQKS LSLSPGK

H39           GQPREPQVYT LPPSRDELTK NQVSLTCLVK GFYPSDIAVE WESNGQPENN
SEQ ID NO: 44 YKTTPPVLDS DGSFFLYSKL TVDKSRWQEG NVFSCSVMHE ALHNHYTQKS LSLSPGK
```

In addition, compositions of the respective reagents are as follows.

TABLE 13

| SDS sample buffer solution | | |
|---|---|---|
| Tris | Sigma-Aldrich Co. LLC | 125 mM |
| SDS | Wako Pure Chemical Corporation | 4% |
| Sucrose | Wako Pure Chemical Corporation | 10% |
| Bromophenol blue | Nacalai Tesque Inc, | 0.01% |
| DTT | Sigma-Aldrich Co. LLC | 200 mM |
| SDS electrophoresis buffer solution | | |
| Tris | Sigma-Aldrich Co. LLC | 3.03 g/L |
| Glycine | Wako Pure Chemical Corporation | 14.4 g/L |
| SDS | Wake Pure Chemical Corporation | 1.0 g/L |
| Transfer buffer solution | | |
| Tris | Sigma-Aldrich Co. LLC | 3.03 g/L |
| Glycine | Wako Pure Chemical Corporation | 14.1 g/L |
| SDS | Wako Pure Chemical Corporation | 0.1 g/L |
| PBST | | |
| Sodium dihydrogen phosphate | Wako Pure Chemical Corporation | 10 mM |
| Sodium chloride | Wako Pure Chemical Corporation | 150 mM |
| Polyoxyethylene (20) sorbitan monolaurate pH7.4 | Wako Pure Chemical Corporation | 0.05% |
| Membrane blocking buffer solution | | |
| Sodium dihydrogen phosphate | Wako Pure Chemical Corporation | 10 mM |
| Sodium chloride | Wako Pure Chemical Corporation | 150 mM |
| Polyoxyethylene (20) sorbitan monolaurate | Wako Pure Chemical Corporation | 0.05% |
| Skim milk pH7.4 | Wako Pure Chemical Corporation | 5% |

INDUSTRIAL APPLICABILITY

As described in detail above, according to the immunoassay method of the present invention, a substance of interest can be specifically and accurately assayed while excluding influence of competitive substances (IgG1 to 3) in a reaction system by means of an antibody with high reactivity and selectivity to a substance of interest (human IgG4). With an anti-human IgG4 antibody of the present invention, human IgG4 in a sample can be specifically detected and assayed, and it is extremely effective in the field of a diagnosis or a clinical examination for an IgG4-related disease.

Sequence Listing

The invention claimed is:

1. A monoclonal antibody specifically binding to human IgG4, wherein the monoclonal antibody binds to:
the region consisting of the amino acid sequence at positions 221 to 274 of the human IgG4 heavy chain constant region represented by SEQ ID NO: 4,
the region consisting of the amino acid sequence at positions 275 to 327 of the human IgG4 heavy chain constant region represented by SEQ ID NO: 4, and
glutamic acid at position 299 of the human IgG4 heavy chain constant region represented by SEQ ID NO: 4.

2. The monoclonal antibody according to claim 1, wherein the monoclonal antibody binds to the human IgG4 with a dissociation constant of from $1.1 \times 10^{-9}$ to $3.0 \times 10^{-10}$ or less.

3. A monoclonal antibody against human IgG4, comprising a heavy chain variable region and a light chain variable region,
wherein complementarity determining regions (CDR) 1, 2, and 3 of the heavy chain variable region consist of amino acid sequences represented by SEQ ID NOS: 9, 10, and 11, respectively, and CDRs 1, 2, and 3 of the light chain variable region consist of amino acid sequences represented by SEQ ID NOS: 12, 13, and 14, respectively.

4. The monoclonal antibody according to claim 3, wherein the heavy chain variable region comprises an amino acid sequence of SEQ ID NO: 5, and the light chain variable region comprises an amino acid sequence of SEQ ID NO: 6.

5. The monoclonal antibody according to claim 4, wherein the monoclonal antibody is produced by a hybridoma Ma14-08.

6. A bivalent antibody molecule or a bivalent antibody fragment comprising two antigen binding sites of the monoclonal antibody according to claim 1.

7. The antibody fragment according to claim 6, wherein the antibody fragment is $F(ab')_2$.

8. A kit for detecting human IgG4, comprising the monoclonal antibody according to claim 1, or the bivalent antibody molecule or the bivalent antibody fragment comprising two antigen binding sites of the monoclonal antibody.

9. The kit according to claim 8, wherein the kit is for a diagnosis of an IgG4-related disease.

10. A method of producing a monoclonal antibody specifically binding to human IgG4 comprising:
selecting, from monoclonal antibodies binding to human IgG4, an antibody which binds to:
the region consisting of the amino acid sequence at positions 221 to 274 of the human IgG4 heavy chain constant region represented by SEQ ID NO: 4,
the region consisting of the amino acid sequence at positions 275 to 327 of the human IgG4 heavy chain constant region represented by SEQ ID NO: 4, and
glutamic acid at position 299 of the human IgG4 heavy chain constant region represented by SEQ ID NO: 4.

11. A method for detecting human IgG4 in a sample comprising:
contacting the sample with:
the monoclonal antibody according to claim 1, or
a bivalent antibody molecule or the bivalent antibody fragment comprising two antigen binding sites of the monoclonal antibody; and
detecting the human IgG4 in the sample.

12. The method according to claim 11, wherein the method is an immunological particle agglutination inhibition method.

13. The method according to claim 12, wherein the human IgG4 in the sample is detected by:
(1) binding the human IgG4 in the sample to the monoclonal antibody or the bivalent antibody molecule or the bivalent antibody fragment;
(2) adding an insoluble carrier on which human IgG4 or a peptide fragment thereof is immobilized to cause an agglutination reaction between the insoluble carrier and the monoclonal antibody or the bivalent antibody molecule or the bivalent antibody fragment that is not bound to the human IgG4 in the sample; and
(3) detecting the agglutinated insoluble carrier.

14. The method according to claim 11, wherein the method is performed to assist a diagnosis of an IgG4-related disease.

15. A kit for the method according to claim 13, the kit comprising:
(1) the monoclonal antibody, or the bivalent antibody molecule or the bivalent antibody fragment;
(2) an isolated human IgG4 or a peptide fragment thereof; and
(3) an insoluble carrier.

16. The kit according to claim 15, wherein (2) the isolated human IgG4 or the peptide fragment thereof is adsorbed on (3) the insoluble carrier.

17. The kit according to claim 15, wherein (3) the insoluble carrier is a latex particle.

18. A monoclonal antibody against human IgG4, comprising a heavy chain variable region and a light chain variable region, wherein complementarity determining regions (CDRs) 1, 2, and 3 of the heavy chain variable region consist of amino acid sequences represented by SEQ ID NOS: 15, 16, and 17, respectively, and CDRs 1, 2, and 3 of the light chain variable region of the antibody consist of amino acid sequences represented by SEQ ID NOS: 18, 19, and 20, respectively.

19. The monoclonal antibody according to claim 18, wherein the heavy chain variable region comprises an amino acid sequence of SEQ ID NO: 7, and the light chain variable region comprises an amino acid sequence of SEQ ID NO: 8.

20. The monoclonal antibody according to claim 19, wherein the monoclonal antibody is produced by a hybridoma Ma14-09.

21. An isolated peptide consisting of:
the amino acid sequence at positions 221 to 274 of the human IgG4 heavy chain constant region represented by SEQ ID NO: 4,
all or part of the amino acid sequence at positions 275 to 327 of the human IgG4 heavy chain constant region represented by SEQ ID NO: 4,
and having glutamic acid at position 299.

* * * * *

UNITED STATES PATENT AND TRADEMARK OFFICE
CERTIFICATE OF CORRECTION

| | | |
|---|---|---|
| PATENT NO. | : 11,372,001 B2 | Page 1 of 1 |
| APPLICATION NO. | : 16/628217 | |
| DATED | : June 28, 2022 | |
| INVENTOR(S) | : Teruuchi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 309 days.

Signed and Sealed this
Eleventh Day of February, 2025

Coke Morgan Stewart
*Acting Director of the United States Patent and Trademark Office*

SEQUENCE LISTING

```
<160> NUMBER OF SEQ ID NOS: 44

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
```

```
                145                 150                 155                 160
Ala Pro Glu Leu Leu Gly Gly Pro Ser Val Phe Leu Phe Pro Pro Lys
                    165                 170                 175

Pro Lys Asp Thr Leu Met Ile Ser Arg Thr Pro Glu Val Thr Cys Val
                    180                 185                 190

Val Val Asp Val Ser His Glu Asp Pro Glu Val Gln Phe Lys Trp Tyr
                    195                 200                 205

Val Asp Gly Val Glu Val His Asn Ala Lys Thr Lys Pro Arg Glu Glu
                    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                    245                 250                 255

Ala Leu Pro Ala Pro Ile Glu Lys Thr Ile Ser Lys Thr Lys Gly Gln
                    260                 265                 270

Pro Arg Glu Pro Gln Val Tyr Thr Leu Pro Pro Ser Arg Glu Glu Met
                    275                 280                 285

Thr Lys Asn Gln Val Ser Leu Thr Cys Leu Val Lys Gly Phe Tyr Pro
                    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                    325                 330                 335

Tyr Ser Lys Leu Thr Val Asp Lys Ser Arg Trp Gln Gln Gly Asn Ile
                    340                 345                 350

Phe Ser Cys Ser Val Met His Glu Ala Leu His Asn Arg Phe Thr Gln
                    355                 360                 365

Lys Ser Leu Ser Leu Ser Pro Gly Lys
                    370                 375

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140
```

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 122
<212> TYPE: PRT
<213> ORGANISM: Artificial Sequence
<220> FEATURE:
<223> OTHER INFORMATION: MaI4-08 VH

<400> SEQUENCE: 5

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Ile Phe Thr Ser Tyr
            20                  25                  30

Ile Leu His Trp Val Lys Gln Lys Pro Gly Gln Gly Leu Glu Trp Ile
        35                  40                  45

Ala Tyr Ile Asn Pro Tyr Asn Asp Gly Thr Lys Tyr Lys Glu Lys Phe
    50                  55                  60

Lys Gly Lys Gly Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Gly Gly Tyr Gly Asn Tyr Ala Trp Phe Ala Tyr Trp
            100                 105                 110

Gly Pro Gly Thr Leu Val Thr Val Ser Thr
        115                 120

<210> SEQ ID NO 6
<211> LENGTH: 107
<212> TYPE: PRT
<213> ORGANISM: Artificial Sequence
<220> FEATURE:
<223> OTHER INFORMATION: MaI4-08 VL

<400> SEQUENCE: 6

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
                20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Pro
                85                  90                  95

Thr Phe Gly Ala Gly Thr Lys Leu Glu Leu Lys
            100                 105

<210> SEQ ID NO 7
<211> LENGTH: 122
<212> TYPE: PRT
<213> ORGANISM: Artificial Sequence
<220> FEATURE:
<223> OTHER INFORMATION: MaI4-09 VH

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
                20                  25                  30

Val Met His Trp Met Lys Gln Lys Pro Gly Gln Gly Leu Glu Trp Ile
            35                  40                  45

Gly Tyr Ile Asn Pro Tyr Asn Asp Gly Thr Arg Tyr Asn Glu Lys Phe
    50                  55                  60

Gln Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Thr Arg Ser Phe Tyr Tyr Gly Asn Ser His Val Leu Phe Ala Tyr Trp
            100                 105                 110

Gly Gln Gly Thr Leu Val Thr Val Ser Ala
            115                 120

<210> SEQ ID NO 8
<211> LENGTH: 107
<212> TYPE: PRT
<213> ORGANISM: Artificial Sequence
<220> FEATURE:
<223> OTHER INFORMATION: MaI4-09 VL

<400> SEQUENCE: 8

Asp Ile Lys Met Thr Gln Ser Pro Ser Ser Ile Tyr Pro Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
```

```
               65                  70                  75                  80
Glu Asp Met Gly Ile Tyr His Cys Leu Gln Tyr Asp Glu Leu Pro Tyr
                        85                  90                  95

Thr Phe Gly Gly Gly Thr Thr Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: MaI4-08 HCDR1

<400> SEQUENCE: 9

Ser Tyr Ile Leu His
1               5

<210> SEQ ID NO 10
<211> LENGTH: 17
<212> TYPE: PRT
<213> ORGANISM: Artificial Sequence
<220> FEATURE:
<223> OTHER INFORMATION: MaI4-08 HCDR2

<400> SEQUENCE: 10

Tyr Ile Asn Pro Tyr Asn Asp Gly Thr Lys Tyr Lys Glu Lys Phe Lys
1               5                   10                  15

Gly

<210> SEQ ID NO 11
<211> LENGTH: 13
<212> TYPE: PRT
<213> ORGANISM: Artificial Sequence
<220> FEATURE:
<223> OTHER INFORMATION: MaI4-08 HCDR3

<400> SEQUENCE: 11

Ser Gly Gly Gly Tyr Gly Asn Tyr Ala Trp Phe Ala Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: MaI4-08 LCDR1

<400> SEQUENCE: 12

Arg Ala Ser Gln Asp Ile Gly Ser Ser Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: MaI4-08 LCDR2

<400> SEQUENCE: 13

Ala Thr Ser Ser Leu Asp Ser
1               5

<210> SEQ ID NO 14
<211> LENGTH: 9
<212> TYPE: PRT
```

<213> ORGANISM: Artificial Sequence
<220> FEATURE:
<223> OTHER INFORMATION: MaI4-08 LCDR3

<400> SEQUENCE: 14

Leu Gln Tyr Ala Ser Tyr Pro Pro Thr
1               5

<210> SEQ ID NO 15
<211> LENGTH: 5
<212> TYPE: PRT
<213> ORGANISM: Artificial Sequence
<220> FEATURE:
<223> OTHER INFORMATION: MaI4-09 HCDR1

<400> SEQUENCE: 15

Ser Ser Val Met His
1               5

<210> SEQ ID NO 16
<211> LENGTH: 17
<212> TYPE: PRT
<213> ORGANISM: Artificial Sequence
<220> FEATURE:
<223> OTHER INFORMATION: MaI4-09 HCDR2

<400> SEQUENCE: 16

Tyr Ile Asn Pro Tyr Asn Asp Gly Thr Arg Tyr Asn Glu Lys Phe Gln
1               5                   10                  15

Gly

<210> SEQ ID NO 17
<211> LENGTH: 13
<212> TYPE: PRT
<213> ORGANISM: Artificial Sequence
<220> FEATURE:
<223> OTHER INFORMATION: MaI4-09 HCDR3

<400> SEQUENCE: 17

Ser Phe Tyr Tyr Gly Asn Ser His Val Leu Phe Ala Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: MaI4-09 LCDR1

<400> SEQUENCE: 18

Lys Ala Ser Gln Asp Ile Asn Ser Tyr Leu Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: MaI4-09 LCDR2

<400> SEQUENCE: 19

Arg Ala Asn Arg Leu Val Asp
1               5

<210> SEQ ID NO 20
<211> LENGTH: 9

```
<212> TYPE: PRT
<213> ORGANISM: Artificial Sequence
<220> FEATURE:
<223> OTHER INFORMATION: MaI4-09 LCDR3

<400> SEQUENCE: 20

Leu Gln Tyr Asp Glu Leu Pro Tyr Thr
1               5

<210> SEQ ID NO 21
<211> LENGTH: 366
<212> TYPE: DNA
<213> ORGANISM: Artificial Sequence
<220> FEATURE:
<223> OTHER INFORMATION: MaI4-08 VH

<400> SEQUENCE: 21
gaggtccagc tgcagcagtc tggacctgaa ctggtaaagc ctggggcttc agtgaagatg      60
tcctgcaagg cttctggata catattcact agctatattt tgcactgggt gaagcagaag     120
cctgggcagg gccttgagtg gattgcatat attaatcctt acaatgatgg tactaagtac     180
aaagagaagt tcaagggcaa ggcacactg acttcagaca atcctccag cacagcctac       240 atggagctca gcagcctgac ctctgaggac tctgcggtct attactgtgc aagatcagga     300
ggagggtatg gtaactacgc tggttttgct tactggggcc agggactct ggtcactgtc      360 tctaca                                                                366

<210> SEQ ID NO 22
<211> LENGTH: 321
<212> TYPE: DNA
<213> ORGANISM: Artificial Sequence
<220> FEATURE:
<223> OTHER INFORMATION: MaI4-08 VL

<400> SEQUENCE: 22
gacatccaga tgacccagtc tccatcctcc ttatctgcct ctctgggaga aagagtcagt      60
ctcacttgtc gggcaagtca ggacattggt agtagcttaa actggcttca gcaggaacca    120
gatggaacta ttaaacgcct gatctacgcc acatccagtt tagattctgg tgtccccaaa    180
aggttcagtg gcagtaggtc tgggtcagat tattctctca ccatcagcag ccttgagtct    240
gaagattttg tagactatta ctgtctacaa tatgctagtt atcctcccac gttcggtgct    300
gggaccaagc tggagctgaa a                                               321

<210> SEQ ID NO 23
<211> LENGTH: 366
<212> TYPE: DNA
<213> ORGANISM: Artificial Sequence
<220> FEATURE:
<223> OTHER INFORMATION: MaI4-09 VH

<400> SEQUENCE: 23
gaggtccagc tgcagcagtc tggacctgag ctggtaaagc ctggggcttc agtgaagatg      60
tcctgcaagg cttctggata cacattcact agctctgtta tgcactggat gaagcagaag    120
cctgggcagg gccttgagtg gattggatat attaatcctt acaatgatgg tactagatac    180
aatgagaagt tccaaggcaa ggccacactg acttcagaca atcctccaa cacagcctac     240 atggagctca gcagcctgac ctctgaggac tctgcggtct attactgtac aagatcattc    300
tactatggta actcccacgt cctgttttgct tactggggcc aagggactct ggtcactgtc   360
tctgca                                                                366
```

<210> SEQ ID NO 24
<211> LENGTH: 321
<212> TYPE: DNA
<213> ORGANISM: Artificial Sequence
<220> FEATURE:
<223> OTHER INFORMATION: MaI4-09 VL

<400> SEQUENCE: 24

```
gacatcaaga tgacccagtc tccatcttcc atatatccat ctctaggaga gagagtcact    60
atcacttgca aggcgagtca ggacattaat agttatttaa gttggttcca gcagaaacca   120
gggaaatctc cgaagaccct gatctatcgt gcaaacagat tggtagatgg ggtcccatct   180
aggttcagtg gcagtggatc tgggcaagat tattctctca ccatcagcag cctggaatat   240
gaagatatgg gaatttatca ttgtctacag tatgatgagc ttccgtacac gttcggaggg   300
gggaccacgc tggaaataaa a                                             321
```

<210> SEQ ID NO 25
<211> LENGTH: 274
<212> TYPE: PRT
<213> ORGANISM: Artificial Sequence
<220> FEATURE:
<223> OTHER INFORMATION: H2

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp

-continued

```
                245                 250                 255
Ile Ala Val Glu Trp Glu Ser Asn Gly Gln Pro Glu Asn Asn Tyr Lys
            260                 265                 270
Thr Thr
```

<210> SEQ ID NO 26
<211> LENGTH: 220
<212> TYPE: PRT
<213> ORGANISM: Artificial Sequence
<220> FEATURE:
<223> OTHER INFORMATION: H3

<400> SEQUENCE: 26

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys
    210                 215                 220
```

<210> SEQ ID NO 27
<211> LENGTH: 165
<212> TYPE: PRT
<213> ORGANISM: Artificial Sequence
<220> FEATURE:
<223> OTHER INFORMATION: H4

<400> SEQUENCE: 27

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
```

```
                    50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His
                165

<210> SEQ ID NO 28
<211> LENGTH: 110
<212> TYPE: PRT
<213> ORGANISM: Artificial Sequence
<220> FEATURE:
<223> OTHER INFORMATION: H5

<400> SEQUENCE: 28

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Ser Cys Pro
                100                 105                 110

<210> SEQ ID NO 29
<211> LENGTH: 55
<212> TYPE: PRT
<213> ORGANISM: Artificial Sequence
<220> FEATURE:
<223> OTHER INFORMATION: H6

<400> SEQUENCE: 29

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala
        50                  55

<210> SEQ ID NO 30
<211> LENGTH: 272
```

<212> TYPE: PRT
<213> ORGANISM: Artificial Sequence
<220> FEATURE:
<223> OTHER INFORMATION: H7

<400> SEQUENCE: 30

Val Leu Gln Ser Ser Gly Leu Tyr Ser Leu Ser Ser Val Val Thr Val
1               5                   10                  15

Pro Ser Ser Leu Gly Thr Lys Thr Tyr Thr Cys Asn Val Asp His
            20                  25                  30

Lys Pro Ser Asn Thr Lys Val Asp Lys Arg Val Glu Ser Lys Tyr Gly
            35                  40                  45

Pro Pro Cys Pro Ser Cys Pro Ala Pro Glu Phe Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Asp Val Ser Gln Glu Asp Pro
                85                  90                  95

Glu Val Gln Phe Asn Trp Tyr Val Asp Gly Val Glu Val His Asn Ala
                100                 105                 110

Lys Thr Lys Pro Arg Glu Glu Gln Phe Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Gly Leu Pro Ser Ser Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Gln Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Arg Leu Thr Val Asp Lys Ser
225                 230                 235                 240

Arg Trp Gln Glu Gly Asn Val Phe Ser Cys Ser Val Met His Glu Ala
                245                 250                 255

Leu His Asn His Tyr Thr Gln Lys Ser Leu Ser Leu Ser Leu Gly Lys
            260                 265                 270

<210> SEQ ID NO 31
<211> LENGTH: 217
<212> TYPE: PRT
<213> ORGANISM: Artificial Sequence
<220> FEATURE:
<223> OTHER INFORMATION: H8

<400> SEQUENCE: 31

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

```
Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 32
<211> LENGTH: 162
<212> TYPE: PRT
<213> ORGANISM: Artificial Sequence
<220> FEATURE:
<223> OTHER INFORMATION: H9

<400> SEQUENCE: 32

Asn Ala Lys Thr Lys Pro Arg Glu Glu Gln Phe Asn Ser Thr Tyr Arg
  1               5                  10                  15

Val Val Ser Val Leu Thr Val Leu His Gln Asp Trp Leu Asn Gly Lys
                 20                  25                  30

Glu Tyr Lys Cys Lys Val Ser Asn Lys Gly Leu Pro Ser Ser Ile Glu
             35                  40                  45

Lys Thr Ile Ser Lys Ala Lys Gly Gln Pro Arg Glu Pro Gln Val Tyr
 50                  55                  60

Thr Leu Pro Pro Ser Gln Glu Glu Met Thr Lys Asn Gln Val Ser Leu
 65                  70                  75                  80

Thr Cys Leu Val Lys Gly Phe Tyr Pro Ser Asp Ile Ala Val Glu Trp
                 85                  90                  95

Glu Ser Asn Gly Gln Pro Glu Asn Asn Tyr Lys Thr Thr Pro Pro Val
            100                 105                 110

Leu Asp Ser Asp Gly Ser Phe Phe Leu Tyr Ser Arg Leu Thr Val Asp
        115                 120                 125

Lys Ser Arg Trp Gln Glu Gly Asn Val Phe Ser Cys Ser Val Met His
    130                 135                 140

Glu Ala Leu His Asn His Tyr Thr Gln Lys Ser Leu Ser Leu Ser Leu
145                 150                 155                 160

Gly Lys

<210> SEQ ID NO 33
<211> LENGTH: 107
<212> TYPE: PRT
<213> ORGANISM: Artificial Sequence
<220> FEATURE:
```

```
<223> OTHER INFORMATION: H10

<400> SEQUENCE: 33

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 34
<211> LENGTH: 53
<212> TYPE: PRT
<213> ORGANISM: Artificial Sequence
<220> FEATURE:
<223> OTHER INFORMATION: H11

<400> SEQUENCE: 34

Pro Pro Val Leu Asp Ser Asp Gly Ser Phe Phe Leu Tyr Ser Arg Leu
1               5                   10                  15

Thr Val Asp Lys Ser Arg Trp Gln Glu Gly Asn Val Phe Ser Cys Ser
            20                  25                  30

Val Met His Glu Ala Leu His Asn His Tyr Thr Gln Lys Ser Leu Ser
        35                  40                  45

Leu Ser Leu Gly Lys
    50

<210> SEQ ID NO 35
<211> LENGTH: 122
<212> TYPE: PRT
<213> ORGANISM: Artificial Sequence
<220> FEATURE:
<223> OTHER INFORMATION: H12

<400> SEQUENCE: 35

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys
```

-continued

```
                115                 120

<210> SEQ ID NO 36
<211> LENGTH: 107
<212> TYPE: PRT
<213> ORGANISM: Artificial Sequence
<220> FEATURE:
<223> OTHER INFORMATION: H31

<400> SEQUENCE: 36

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: H32

<400> SEQUENCE: 37

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: H33

<400> SEQUENCE: 38

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30
```

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: H34

<400> SEQUENCE: 39

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: H35

<400> SEQUENCE: 40

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

```
<210> SEQ ID NO 41
<211> LENGTH: 107
<212> TYPE: PRT
<213> ORGANISM: Artificial Sequence
<220> FEATURE:
<223> OTHER INFORMATION: H36

<400> SEQUENCE: 41

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: H37

<400> SEQUENCE: 42

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: H38

<400> SEQUENCE: 43

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
        50              55                  60

Phe Leu Tyr Ser Lys Leu Thr Val Asp Lys Ser Arg Trp Gln Gln Gly
65              70                  75                      80

Asn Val Phe Ser Cys Ser Val Met His Glu Ala Leu His Asn His Tyr
                85              90                  95

Thr Gln Lys Ser Leu Ser Leu Ser Pro Gly Lys
            100             105

<210> SEQ ID NO 44
<211> LENGTH: 107
<212> TYPE: PRT
<213> ORGANISM: Artificial Sequence
<220> FEATURE:
<223> OTHER INFORMATION: H39

<400> SEQUENCE: 44

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
        50              55                  60

Phe Leu Tyr Ser Lys Leu Thr Val Asp Lys Ser Arg Trp Gln Glu Gly
65              70                  75                      80

Asn Val Phe Ser Cys Ser Val Met His Glu Ala Leu His Asn His Tyr
                85              90                  95

Thr Gln Lys Ser Leu Ser Leu Ser Pro Gly Lys
            100             105
```